United States Patent
Yao et al.

(10) Patent No.: US 9,244,086 B2
(45) Date of Patent: Jan. 26, 2016

(54) SAMPLE ANALYZING SYSTEM, SAMPLE ANALYZER, AND MANAGEMENT METHOD OF SAMPLE ANALYZING SYSTEM

(71) Applicant: SYSMEX CORPORATION, Kobe-shi, Hyogo (JP)

(72) Inventors: Syunsuke Yao, Kobe (JP); Shiro Kuwaoka, Kobe (JP); Taisuke Nishida, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 374 days.

(21) Appl. No.: 13/851,677

(22) Filed: Mar. 27, 2013

(65) Prior Publication Data
US 2013/0260414 A1 Oct. 3, 2013

(30) Foreign Application Priority Data
Mar. 28, 2012 (JP) ................................. 2012-073882

(51) Int. Cl.
*G01N 21/00* (2006.01)
*G01N 35/00* (2006.01)
*G01N 33/00* (2006.01)

(52) U.S. Cl.
CPC .... *G01N 35/00712* (2013.01); *G01N 35/00603* (2013.01)

(58) Field of Classification Search
CPC ............... G01N 35/0063; G01N 35/00732; G01N 35/02; G01N 35/025; G01N 35/026; G01N 35/1004
USPC ............................................................ 422/73
See application file for complete search history.

(56) References Cited

U.S. PATENT DOCUMENTS

| | | | |
|---|---|---|---|
| 2007/0231208 A1* | 10/2007 | Tanaka et al. | 422/67 |
| 2008/0106713 A1* | 5/2008 | Katano et al. | 355/30 |
| 2011/0189053 A1 | 8/2011 | Tatsutani et al. | |

FOREIGN PATENT DOCUMENTS

| | | |
|---|---|---|
| CN | 102192996 A | 9/2011 |
| JP | 2008-032493 A | 2/2008 |

OTHER PUBLICATIONS

Dewitte, Robert et al. Automated System for Sample Preparation and Analysis. May 3, 2012. WO 2012/058632 A1 (see attached).*

* cited by examiner

*Primary Examiner* — Jill Warden
*Assistant Examiner* — Brittany Fisher
(74) *Attorney, Agent, or Firm* — Sughrue Mion, PLLC

(57) ABSTRACT

A sample analyzing system comprising: a first sample analyzer including a first measurement unit for measuring a sample and a first control unit for controlling the first measurement unit; and a second sample analyzer including a second measurement unit for measuring the sample and a second control unit for controlling the second measurement unit; wherein the first control unit is configured to transmit an activation signal for activating the second sample analyzer when a predetermined condition is met for the first sample analyzer; and the second control unit is configured to activate the second sample analyzer when the activation signal is received.

27 Claims, 15 Drawing Sheets

FIG. 5

| REAGENT | REMAINING AMOUNT |
|---|---|
| DILUTED SOLUTION | 105 |
| HEMOGLOBIN HEMOLYTIC AGENT | 73 |
| WHITE BLOOD CELLS CLASSIFYING HEMOLYTIC AGENT | 215 |
| WHITE BLOOD CELLS CLASSIFYING STAINING FLUID | 124 |

| |
|---|
| LASER OUTPUT ABNORMALITY |
| WATER LEAKAGE DETECTION |
| ⋮ |

| ERROR | USAGE SET VALUE |
|---|---|
| PRESSURE ABNORMALITY | 1 |
| NO REMAINING AMOUNT OF REAGENT | 1 |
| FULL DISCARDING LIQUID | 0 |
| ⋮ | ⋮ |

FIG. 11

SETTING INFORMATION INSTRUCTING MODE SETTING

<FORMAT> SU ¥ MODE INFORMATION
         ↖
          MODE SETTING INSTRUCTING IDENTIFIER

· CASE OF MANUAL MODE
    SU ¥ Manual
· CASE OF SAMPLER MODE
    SU ¥ Sampler

SETTING INFORMATION INSTRUCTING ORDER REGISTRATION

<FORMAT> JR ¥ RACK NUMBER ¥ POSITION OF SAMPLE CONTAINER ¥
        ↖ SAMPLE NUMBER ¥ PATIENT ID ¥ MEASUREMENT ITEM^
         ORDER PRESENCE/ABSENCE···
         ORDER REGISTRATION INSTRUCTING IDENTIFIER

· EXAMPLE
  JR ¥ 10001 ¥ 01 ¥ 20111124 101 Sampler001 ¥ Patient ID000001 ¥ WBC^1 ¥ HGB^1 ¥ HCT^0···

FIG. 12

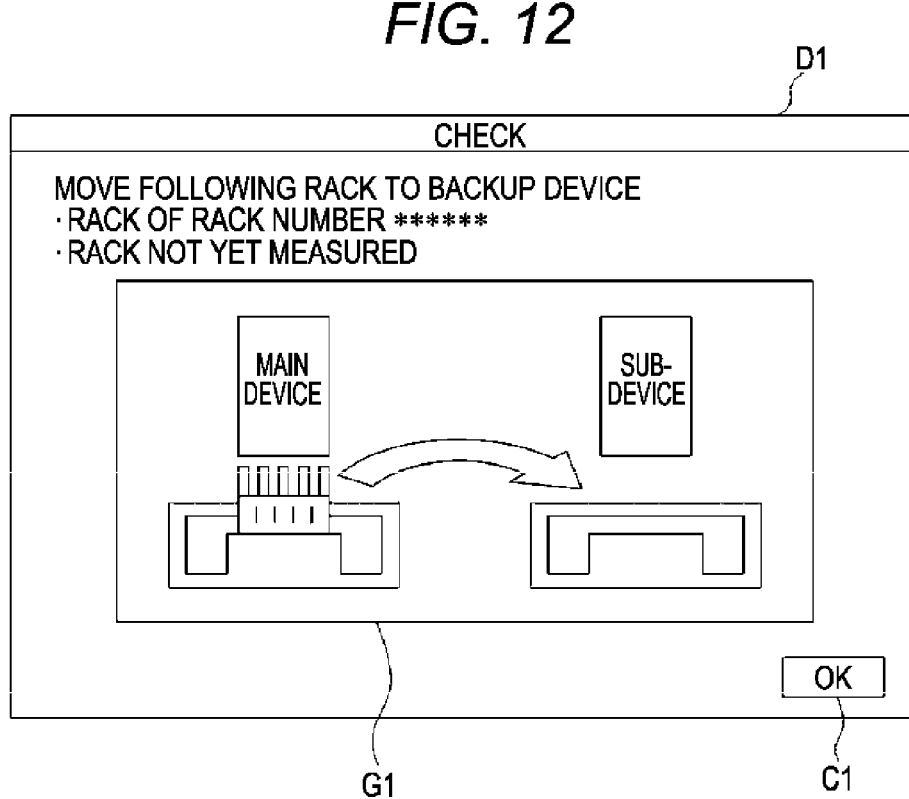

SAMPLE ANALYZING SYSTEM, SAMPLE ANALYZER, AND MANAGEMENT METHOD OF SAMPLE ANALYZING SYSTEM

FIELD OF THE INVENTION

The present invention relates to a sample analyzing system and a sample analyzer for analyzing a sample collected from a human or an animal such as a blood sample, a urine sample, or the like, as well as a management method of the sample analyzing system.

BACKGROUND

A sample analyzer for analyzing blood or urine such as a blood cell counting device, a blood coagulation measurement device, an immune analyzer, a biochemical analyzer, a urine analyzer, and the like is known.

In a facility such as hospitals, test centers, and the like where a plurality of the same type of sample analyzers are installed, the sample analyzer to be used is switched every day or every week, for example, and when using some of the plurality of installed sample analyzers, the other sample analyzers are not used. In this case, the sample analyzers that are not used are installed for backup, and thus are in a shutdown state. When abnormality occurs in the sample analyzer being used or when there are a large number of samples and a great amount time is required to complete the analysis of all the samples with the sample analyzers being used, the sample analyzer for backup is activated and used for sample analysis.

For example, in the sample analyzer disclosed in Japanese Laid-Open Patent Publication No. 2008-32493, when abnormality occurs in the sample analyzer, the occurrence of abnormality is displayed on a screen of the sample analyzer to notify the user. The user manually activates the backup sample analyzer when confirming the occurrence of abnormality of the sample analyzer or when determining that the sample analysis takes time with only the operating sample analyzer.

When switching the sample analyzer to be used by time, the operator shuts down the sample analyzer being used by hand and activates the sample analyzer that was not being used when a switching time is reached.

However, the operator needs to move to the place where the backup sample analyzer is installed to perform the activating operation in order to activate the backup sample analyzer. The backup sample analyzer may not be installed near the sample analyzer being used, in which case the backup sample analyzer cannot be efficiently activated and the processing may stagnate during such time. If the operator neither notice the abnormality of the device nor notice that a great number of samples is registered beyond the processing performance of the analyzer, the backup sample analyzer may not be activated for a long period of time and the sample processing may stagnate.

When switching the sample analyzer to use by time as well, the operator cannot efficiently carry out the switching operation if the sample analyzer to be used next is not installed near the sample analyzer being used.

SUMMARY OF THE INVENTION

The scope of the present invention is defined solely by the appended claims, and is not affected to any degree by the statements within this summary.

A first aspect of the present invention is a sample analyzing system comprising: a first sample analyzer including a first measurement unit for measuring a sample and a first control unit for controlling the first measurement unit; and a second sample analyzer including a second measurement unit for measuring the sample and a second control unit for controlling the second measurement unit; wherein the first control unit is configured to transmit an activation signal for activating the second sample analyzer when a predetermined condition is met for the first sample analyzer; and the second control unit is configured to activate the second sample analyzer when the activation signal is received.

A second aspect of the present invention is a sample analyzing system comprising: a first sample analyzer including a first measurement unit for measuring a sample and a first control unit for controlling the first measurement unit; a second sample analyzer including a second measurement unit for measuring the sample and a second control unit for controlling the second measurement unit; and a management device including a third control unit capable of communicating with the first control unit and the second control unit; wherein the third control unit is configured to transmit an activation signal for activating the second sample analyzer when a predetermined condition is met for the first sample analyzer; and the second control unit is configured to activate the second sample analyzer when the activation signal is received.

A third aspect of the present invention is a sample analyzing system comprising a measurement unit for measuring a sample and a control unit for controlling the measurement unit; wherein the control unit is configured to transmit an activation signal for activating another sample analyzer when a predetermined condition is met for the sample analyzer.

A forth aspect of the present invention is a method of managing a sample analyzing system including a main sample analyzer and a sub-sample analyzer, the method comprising the steps of having the main sample analyzer in an operating state and the sub-sample analyzer in a standby state; detecting a trouble of the main sample analyzer in the operating state; and changing the state of the sub-sample analyzer from the standby state to the operating state when the trouble of the main sample analyzer is detected.

BRIEF DESCRIPTION OF THE DRAWINGS

FIG. 5 is a schematic view showing a configuration of reagent remaining amount information;

FIG. 6 is a schematic view showing a configuration of a first abnormality database;

FIG. 7 is a schematic view showing a configuration of a second abnormality database;

FIG. 11 is a view describing setting information;

FIG. 12 is a view showing one example of a sub-device activation notifying screen;

DETAILED DESCRIPTION OF THE PREFERRED EMBODIMENTS

The preferred embodiments of the present invention will be described hereinafter with reference to the drawings.

First Embodiment

Configuration of Sample Analyzing System

Figure 1:
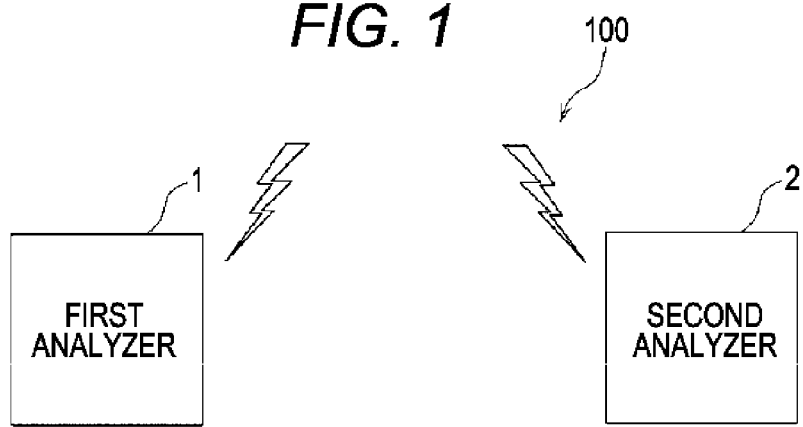
FIG. 1 is a schematic view showing an overall configuration of a sample analyzing system according to a first embodiment.

FIG. 1 is a schematic view showing an overall configuration of a sample analyzing system according to the present embodiment. A sample analyzing system 100 according to the present embodiment includes a first sample analyzer 1 and a second sample analyzer 2. The sample analyzing system 100 is installed in one of the facilities such as the hospital, the test center, or the like.

The first sample analyzer 1 and the second sample analyzer 2 are the same type of sample analyzer. In other words, the first sample analyzer 1 is a multi-item blood cell analyzer for detecting white blood cells, red blood cells, blood platelets and the like contained in the blood sample and counting each blood cell, and the second sample analyzer 2 is also a multi-item blood cell analyzer.

The first sample analyzer 1 includes a measurement unit 11, a sample transport unit 12 arranged on a front surface side of the measurement unit 11, and an information processing unit 13 capable of controlling the measurement unit 11 and the sample transport unit 12. The first sample analyzer 1 also includes a wireless communication unit 14. The second sample analyzer 2 also includes a wireless communication unit 24. The wireless communication units 14, 24 comply with a common wireless communication standard IEEE 802.11, and can communicate with each other.

Figure 2:
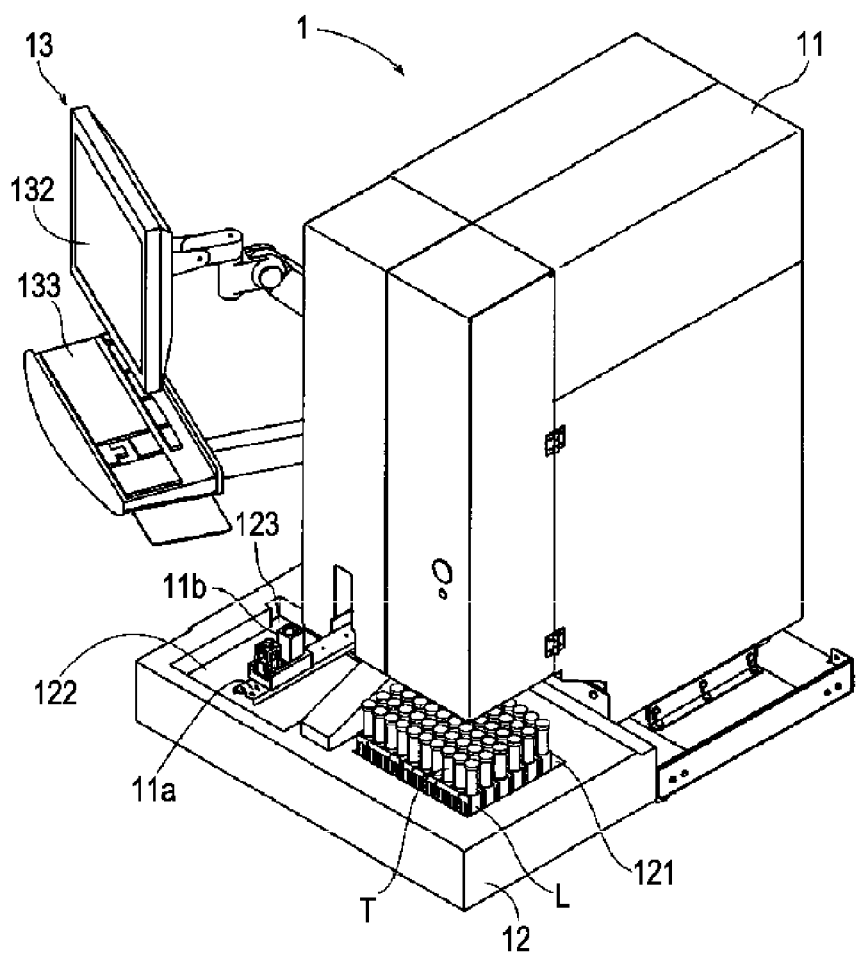
FIG. 2 is a perspective view showing a configuration of a first sample analyzer.

FIG. 2 is a perspective view showing a configuration of the first sample analyzer 1. As shown in FIG. 2, the first sample analyzer 1 transports a sample rack holding a plurality of sample containers with the sample transport unit 12, and aspirates a sample from the sample container and analyzes the sample with the measurement unit 11. The sample container T has a tubular shape with the upper end opened. The sample container T interiorly accommodates a blood sample collected from a patient, and the opening at the upper end is sealed with a lid. A barcode label is attached to a side surface of the sample container T. A barcode indicating a sample ID is printed on the barcode label. The sample rack L can hold ten sample containers T in a line. Each sample container T is held in a perpendicular state (upright position state) in the sample rack L. A barcode label is attached to a side surface of the sample rack L. A barcode indicating a rack ID is printed on the barcode label.

Configuration of First Sample Analyzer

A configuration of the first sample analyzer 1 will be hereinafter described.

Configuration of Measurement Unit

A configuration of a measurement unit will now be described. As shown in FIG. 2, on a front surface of the measurement unit 11 is provided a take-in port for taking in the sample container T to inside the measurement unit 11, and a sample container take-in portion 11a for taking in the sample container T from the sample rack L to the inside of the measurement unit 11 and transporting the sample container T to an aspirating position by a sample aspirating portion. An installing portion 11b, to which the sample container T can be installed, is arranged in the sample container take-in portion 11a. In a sampler mode to be described later, the sample container T transported by the sample transport unit 12 is automatically taken into the measurement unit 11 by the sample container take-in portion 11a, and the sample measurement is carried out. In a manual mode, the sample container take-in portion 11a moves forward from the take-in port, the operator installs the sample container T in the installing portion 11b and turns ON a measurement start switch provided on a front surface of the measurement unit 11, whereby the sample container T is taken into the measurement unit 11 and the sample measurement is carried out.

Figure 3:
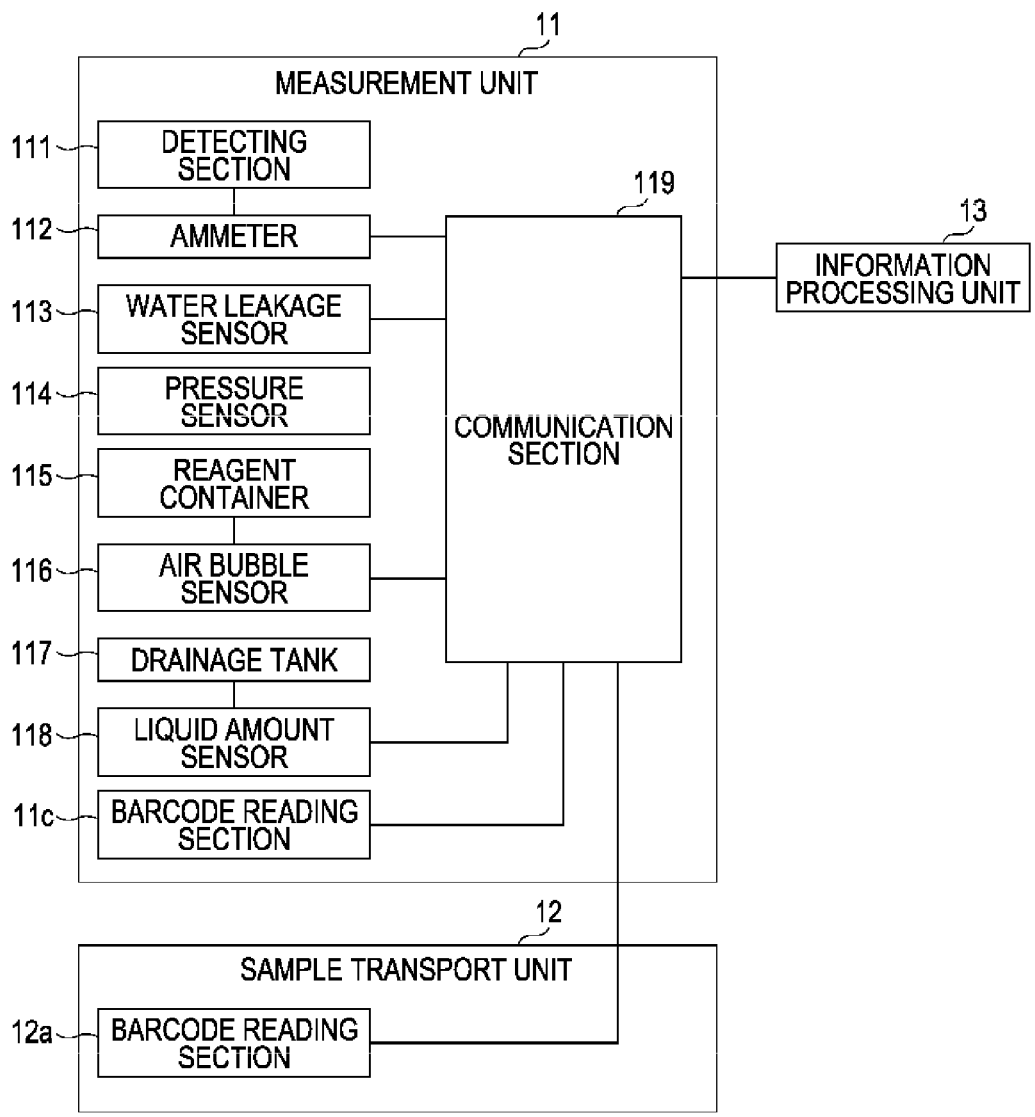
FIG. 3 is a block diagram showing one part of a configuration of a measurement unit of the first sample analyzer.

FIG. 3 is a block diagram showing one part of a configuration of the measurement unit 11. As shown in FIG. 3, the measurement unit 11 includes a detecting section 111, an ammeter 112, a water leakage sensor 113, a pressure sensor 114, a reagent container 115, an air bubble sensor 116, a drainage tank 117, a liquid amount sensor 118, and a communication section 119. The detecting section 111 is configured as an optical detector capable of performing WBC measurement (counting of white blood cells) and DIFF measurement (classification of white blood cells). The detecting section 111 is configured to be able to carry out the detection of WBC (white blood cells), NEUT (neutrophil cells), LYMPH (lymphocytes), EO (eosinocytes), BASO (basocytes), and MONO (monocytes) through a flow cytometry method using a semiconductor laser.

The measurement of the measurement specimen in which staining reagent, hemolytic agent, and diluted solution are mixed is carried out by the detecting section 111, and the obtained measurement data are subjected to analysis processing by the information processing unit 13 to perform the measurement of NEUT, LYMPH, EO, BASO, MONO, and WBC.

The detecting section 111 includes a flow cell, and irradiates the measurement specimen fed to the flow cell with semiconductor laser light. The forward scattered light, the side scattered light, and the side fluorescence generated in this case are received, and the forward scattered light intensity, the side scattered light intensity, and the side fluorescence light intensity are detected. The measurement data including each optical information of the forward scattered light intensity, the side scattered light intensity, and the side fluorescence intensity obtained in such manner is transmitted from the measurement unit 11 to the information processing unit 13, and analyzed by the information processing unit 13.

The ammeter 112 measures the output current of the semiconductor laser irradiating portion of the detecting section 111. The measurement value of the laser output current is provided to the information processing unit 13, and determination is made that laser output abnormality occurred when the laser output current value exceeds a predetermined value.

The water leakage sensor 113 detects the water leakage inside the measurement unit 11. When the water leakage sensor 113 detects the water leakage, the detection signal is provided to the information processing unit 13, and determination is made that the leakage water abnormality occurred.

The pressure sensor 114 detects the pressure at a predetermined area inside the measurement unit 11. The data of the pressure value detected by the pressure sensor is provided to the information processing unit 13, and determination is made that the pressure abnormality occurred when the pressure value deviates from the normal range.

The reagent container 115 contains the reagent (staining reagent, hemolytic agent, diluted solution, etc.) used for the sample measurement. Such reagent container 115 is installed inside the measurement unit 11, and connected to a fluid circuit connecting to the detecting section 111. The air bubble sensor 116 is attached to the distribution line of the reagent connecting to the reagent container. The air bubble sensor 116 detects the air bubbles in the distribution line. When the air bubble sensor 116 detects the air bubbles, the detection signal is provided to the information processing unit 13, and determination is made that reagent remaining amount abnormality of the reagent container 115 occurred.

The drainage tank 117 contains the drainage (mixed solution of used sample and reagent, etc.) produced by the measurement of the sample. A distribution line for the drainage is arranged from the detecting section 111 to the drainage tank 117, so that the drainage produced by the detecting section 111 is discharged to the drainage tank 117.

The liquid amount sensor 118 is installed in the drainage tank 117 to detect the liquid amount of the drainage tank 117. The detection signal of the liquid amount sensor 118 is provided to the information processing unit 13, and determination is made that the drainage abnormality (full drainage) occurred when the liquid amount exceeds a predetermined value.

The communication section 119 is configured by an input/output interface such as USB, IEEE 1394, RS-232C, and the like. The communication section 119 is connected to the ammeter 112, the water leakage sensor 113, the pressure sensor 114, the air bubble sensor 116, and the liquid amount sensor 118, and is configured to receive the signals output from the sensors. The communication section 119 is also connected to the information processing unit 13, so that the information processing unit 13 and the measurement unit 11 can communicate with each other.

A barcode reading section 11c is arranged inside the measurement unit 11. The barcode reading section 11c reads the sample ID from the sample barcode of the sample container T taken into the measurement unit 11. A barcode reading section 12a is connected to the communication section 119, and the read sample ID is provided to the information processing unit 13 through the communication section 119. The information processing unit 13 acquires the measurement order with the sample ID as the key, and the measurement unit 11 is controlled to perform the sample measurement of the item specified in the measurement order. The sample is aspirated from the sample container T, from which the sample ID is read, at inside the measurement unit 11, the sample is mixed with the reagent, and the sample measurement is carried out.

Configuration of Sample Transport Unit

A configuration of the sample transport unit 12 will now be described. As shown in FIG. 2, the sample transport unit 12 is arranged on the front side of the measurement unit 11 of the first sample analyzer 1. Such sample transport unit 12 can transport the sample rack L to supply the sample to the measurement unit 11.

The sample transport unit 12 includes a pre-analysis rack holder 121, which can temporarily hold a plurality of sample racks L that holds the sample container T accommodating the sample before performed with analysis; a post-analysis rack holder 122, which can temporarily hold the plurality of sample racks L that holds the sample container T from which the sample is aspirated by the measurement unit 11, and a rack transporting portion 123 for linearly moving the sample rack L horizontally to traverse the front of the measurement unit 11 and transport the sample rack L received from the pre-analysis rack holder 121 to the post-analysis rack holder 122 to provide the sample to the measurement unit 11. The barcode reading section 12a for reading the rack ID from the rack barcode is arranged proximate to the rack transporting portion 123 of the sample transport unit 12 (see FIG. 3). The barcode reading section 12a is connected to the communication section 119 of the measurement unit 11, and the read rack ID is provided to the information processing unit 13 through the communication section 119. In the sampler mode, the sample rack L set in the pre-analysis rack holder 121 is moved by the rack transporting portion 123, and the rack ID is read from the sample rack L of the rack transporting portion 123 by the rack barcode reading section 12a. The read rack ID is provided to the information processing unit 13. The sample container T at a predetermined position of the rack transporting portion 123 is taken inside the measurement unit 11 by the sample container take-in portion 11a and then the sample is measured. The sample container T after the sample is aspirated is discharged from the measurement unit 11 and returned to the original position of the sample rack L. After the sample is aspirated from all the sample containers held in the sample rack L, the sample rack L is transferred to the post-analysis rack holder 121.

Configuration of Information Processing Unit

Figure 4:
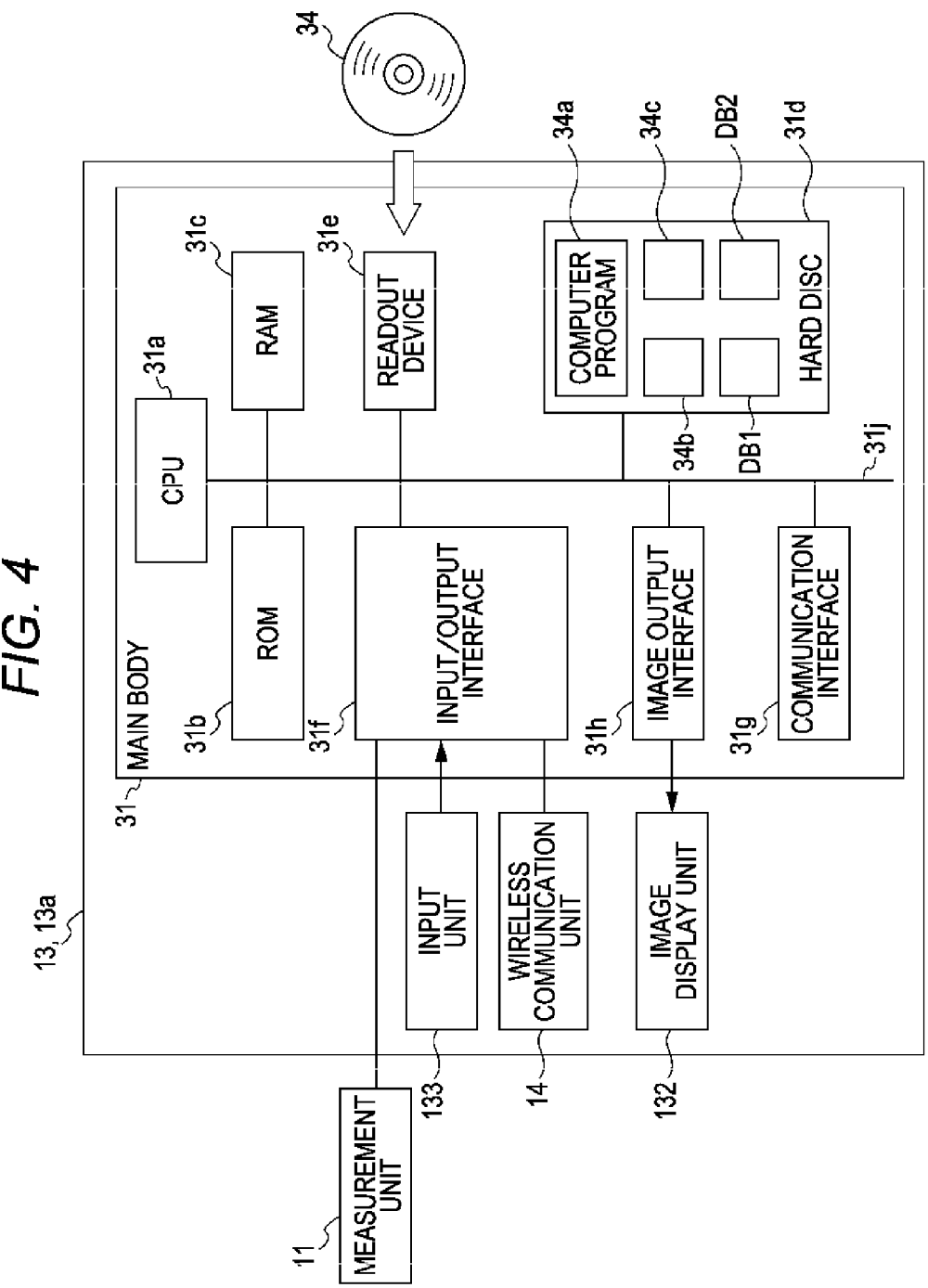
FIG. 4 is a block diagram showing a configuration of the information processing unit of the first sample analyzer.

A configuration of the information processing unit 13 will now be described. The information processing unit 13 is configured by a computer. FIG. 4 is a block diagram showing a configuration of the information processing unit 13. As shown in FIG. 4, a computer 13a includes a main body 31, an image display unit 132, and an input unit 133. The main body 31 includes a CPU 31a, a ROM 31b, a RAM 31c, a hard disc 31d, a readout device 31e, an input/output interface 31f, a communication interface 31g, and an image output interface 31h, where the CPU 31a, the ROM 31b, the RAM 31c, the hard disc 31d, the readout device 31e, the input/output interface 31f, the communication interface 31g and the image output interface 31h are connected by a bus 31j.

The CPU 31a is capable of executing the computer program loaded in the RAM 31c. When the CPU 31a executes the computer program 34a for the sample analysis and for the control for the measurement unit 11 and the sample transport unit 12 to be described later, the computer 13a functions as the information processing unit 13.

The ROM 31b is configured by mask ROM, PROM, EPROM, EEPROM, and the like, and is recorded with computer programs to be executed by the CPU 31a, data used for the same, and the like. The RAM 31c is configured by SRAM, DRAM, and the like. The RAM 31c is used to read out the computer programs 34a recorded on the hard disc 31d. The CPU 31a is used as an operation region of the CPU 31a when the CPU 31a executes the computer program.

The hard disc 31d is installed with various computer programs to be executed by the CPU 31a such as operating system and application program, as well as data used in executing the computer program. The computer program 34a to be described later is also installed in the hard disc 31d.

The read-out device 31e is configured by flexible disc drive, CD-ROM drive, DVD-ROM drive, or the like, and reads the computer programs or data recorded on a portable recording medium 34. The portable recording medium 34 stores the computer program 34a for causing the computer to function as the information processing unit 13, where the computer 13a can read out the computer program 34a from the portable recording medium 34 and install the computer program 34a in the hard disc 31d.

The hard disc 31d is installed with a multi-task operation system such as Windows (registered trademark) manufactured and sold by US Microsoft, for example. In the following description, the computer program 34a according to the present embodiment is assumed to operate on the operating system.

The hard disc 31d stores reagent remaining amount information 34b and the setting information 34c. FIG. 5 is a schematic view showing a configuration of the reagent remaining amount information 34b. The remaining amount of the reagent is stored as the reagent remaining amount information 34b for every type of reagent (diluted solution, white blood cells classification hemolytic agent, white blood cells classification stain fluid). The remaining amount of reagent is represented by the number of measurements indicating the number of times the measurement can be carried out.

As will be described later, when the first sample analyzer 1 is used for sample analysis, and the second sample analyzer 2 is not used for sample analysis for the backup, the second sample analyzer 2 is automatically activated at the occurrence of a specific abnormality in the first sample analyzer 1. That is, the second sample analyzer 2 is activated when a specific abnormality occurs in the first sample analyzer 1, but the second sample analyzer 2 is not activated when an abnormality other than the specific abnormality occurs in the first sample analyzer 1. The hard disc 31d includes a first abnormality database DB1 and a second abnormality database DB2 for storing data defining the abnormality to activate the second sample analyzer.

FIG. 6 is a schematic view showing a configuration of the first abnormality database DB1, and FIG. 7 is a schematic view showing a configuration of the second abnormality database DB2. The first abnormality database DB1 is a database for defining the abnormality to activate the second sample analyzer 2. The first abnormality database DB1 stores in advance information (error code) for identifying the abnormality that requires a serviceman for recovery. For example, the laser output abnormality and the water leakage abnormality are abnormalities that require the serviceman, and such error codes are registered in the first abnormality database DB1. When an abnormality occurs in the first sample analyzer 1, the first abnormality database DB1 is referenced, and the second sample analyzer 2 is automatically activated if the error code of the abnormality that occurred matches the error code registered in the first abnormality database DB1. This is to suppress the sample processing from stagnating as much as possible by activating the second sample analyzer 2 at the occurrence of this type of abnormality since a relatively long time is required for recovery. The abnormality registered in the first abnormality database DB1 cannot be setting changed by a user.

The second abnormality database DB2 is a database that can be setting changed by the user. The second abnormality database DB2 includes a field for storing information (error code) for identifying the abnormality that can be recovered by user alone, and a field for storing information (usage set value) indicating whether or not to use for the activation of the second sample analyzer 2. When activating the second sample analyzer 2 upon occurrence of a corresponding abnormality, the usage set value is set to "1", and when not activating the second sample analyzer 2 upon occurrence of a corresponding abnormality, the usage set value is set to "0". The usage set value can be setting changed by the user. For example, the abnormalities such as pressure abnormality, no remaining amount of reagent, and full discarding liquid are abnormalities that can be handled with the user alone, and such error codes are stored in the second abnormality database DB2. In the example shown in FIG. 7, the usage set value is set to "1" for "pressure abnormality" and "no remaining amount of reagent", and the usage set value is set to "0" for "full discarding liquid". When an abnormality occurs in the first sample analyzer 1, the second abnormality database DB2 is referenced, and the second sample analyzer 2 is automatically activated if the error code of the abnormality that occurred matches the error code registered in the second abnormality database DB2 and the usage set value thereof is "1". If the error code of an abnormality occurring in the first sample analyzer 1 matches the error code registered in the second abnormality database DB2 and the usage set value is "0", the second sample analyzer 2 is not activated. This type of abnormality may be an abnormality that requires a relatively long time for recovery or an abnormality that does not require a relatively long time for recovery according to the facility of the user. In the present embodiment, the user can freely set whether or not to activate the second sample analyzer 2 for each abnormality registered in the second abnormality database DB2.

The input/output interface 31f includes a serial interface such as USB, IEEE1394, and RS-232C; a parallel interface such as SCSI, IDE, and IEEE1284; and an analog interface such as D/A converter and A/D converter. The input/output interface 31f is connected to the input unit 133 including a keyboard and a mouse, and the operator can use the input unit 133 to input data to the computer 13a. The input/output interface 31f is connected to the measurement unit 11 and the sample transport unit 12. The information processing unit 13 can control each of the measurement unit 11 and the sample transport unit 12.

The input/output interface 31f is connected to the wireless communication unit 14. The information processing unit 13 can transmit and receive data with the second sample analyzer 2 through the wireless communication unit 14.

The communication interface 31g is, for example, Ethernet (registered trademark) interface. The communication interface 31g is connected to a host computer (not shown) through a LAN. The computer 13a transmits and receives data with the host computer connected to the LAN using a predetermined communication protocol by means of the communication interface 31g.

The image output interface 31h is connected to the image display unit 132 configured by LCD, CRT, or the like, and is configured to output an image signal corresponding to the image data provided from the CPU 31a to the image display unit 132. The image display unit 132 displays the image (screen) according to the input image signal.

Configuration of Second Sample Analyzer

A configuration of the second sample analyzer 2 will be hereinafter described.

The second sample analyzer 2 is a multi-item blood cell analyzer, same as the first sample analyzer 1. Therefore, the second sample analyzer 2 can perform sample analysis on the measurement item common with the first sample analyzer 1. In other words, the second sample analyzer 2 can measure the NEUT, LYMPH, EO, BASO, MONO, and WBC.

The second sample analyzer 2 also includes a measurement unit 21, a sample transport unit 22, and an information processing unit 23, same as the first sample analyzer 1. The configurations of the measurement unit 21 and the sample transport unit 22 of the second sample analyzer 2 are similar to the configurations of the measurement unit 11 and the sample transport unit 12 of the first sample analyzer 1, and hence the description thereof will be omitted.

Figure 8:
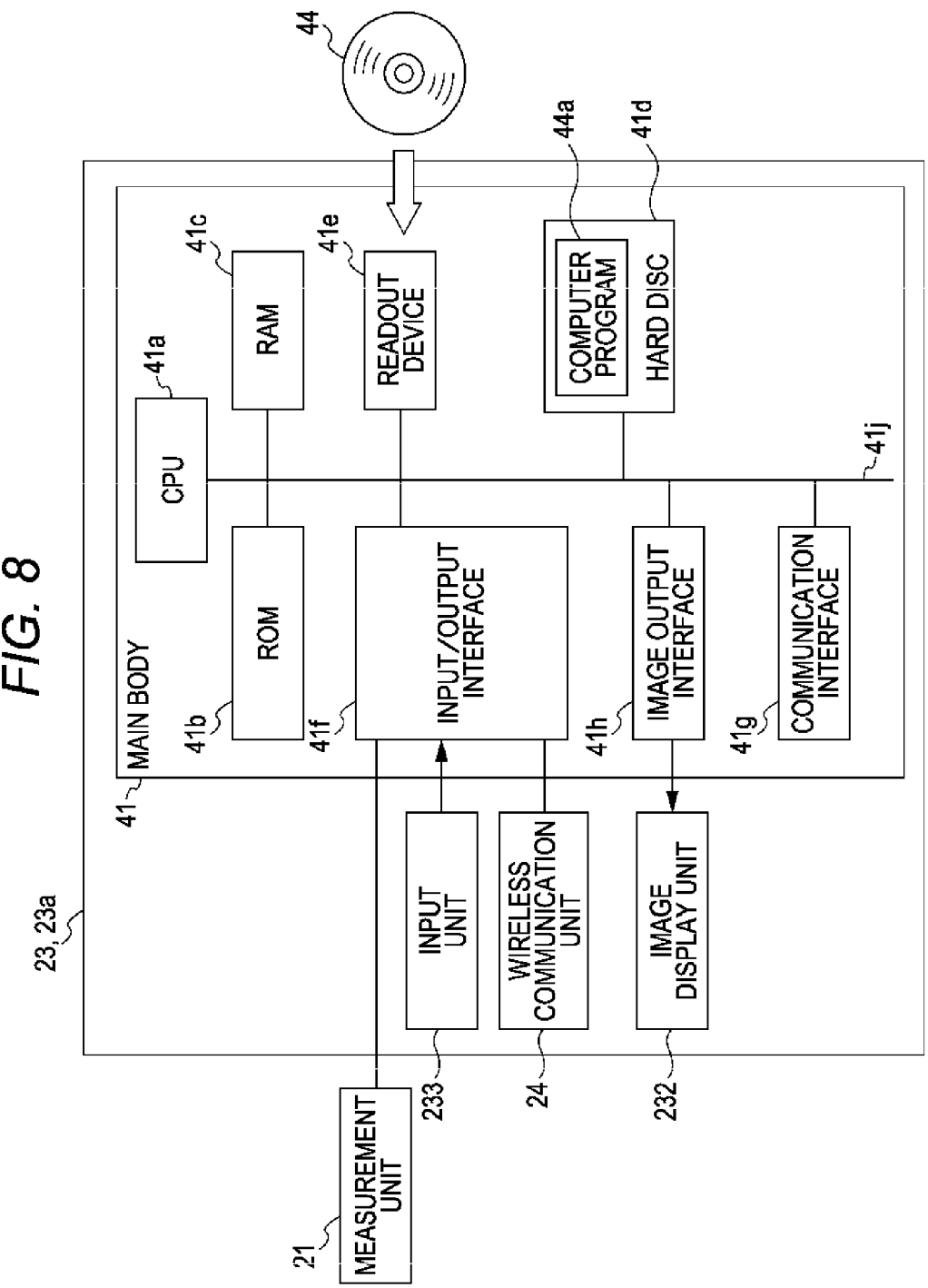
FIG. 8 is a block diagram showing a configuration of the information processing unit of a second sample analyzer.

FIG. 8 is a block diagram showing a configuration of the information processing unit 23 of the second sample analyzer 2. The information processing unit 23 is configured by a computer. As shown in FIG. 8, a computer 23a includes a main body 41, an image display unit 232, and an input unit 233. The main body 41 includes a CPU 41a, a ROM 41b, a RAM 41c, a hard disc 41d, a readout device 41e, an input/output interface 41f, a communication interface 41g, and an image output interface 41h, where the CPU 41a, the ROM 41b, the RAM 41c, the hard disc 41d, the readout device 41e, the input/output interface 41f, the communication interface 41g, and the image output interface 41h are connected with a bus 41j.

The input/output interface 41f includes a serial interface such as USB, IEEE1394, and RS-232C; a parallel interface such as SCSI, IDE, and IEEE1284; and an analog interface such as D/A converter and A/D converter. The input/output interface 41f is connected to the input unit 233 including a keyboard and a mouse, and the operator can use the input unit 233 to input data to the computer 23a. The input/output interface 41f is connected to the measurement unit 21 and the sample transport unit 22. The information processing unit 13 can control each of the measurement unit 21 and the sample transport unit 22.

The input/output interface 41f is connected to the wireless communication unit 24. The information processing unit 23 can transmit and receive data with the first sample analyzer 1 through the wireless communication unit 24. The wireless communication unit 24 can activate the second sample analyzer 2 in a shutdown state by receiving a predetermined activation signal. The shutdown state is a state in which power is not supplied to the measurement unit 21, the sample transport unit 22, and the information processing unit 23, and power is supplied to the input/output interface 41f and the wireless communication unit 24. In this state, the wireless communication unit 24 can receive the activation signal, where the information processing unit 23 is automatically activated through the input/output interface 41f when the wireless communication unit 24 receives the activation signal. When the information processing unit 23 is activated, the measurement unit 21 and the sample transport unit 22 are also activated accordingly and the entire second sample analyzer 2 is activated. In other words, the shutdown state is also a standby state for the second sample analyzer 2 to wait for the reception of the activation signal. When the activation signal is transmitted, the state of the second sample analyzer 2 is changed from the standby state to the operating state.

Other configurations of the information processing unit 23 are similar to the configurations of the information processing unit 13, and thus the description thereof will be omitted.

Configuration of Sample Analyzing System

The operation of the sample analyzing system 100 according to the present embodiment will now be described. Hereinafter, a case in which the first sample analyzer 1 is the sample analyzer (hereinafter also referred to as "main device") that is mainly used, and the second sample analyzer 2 is the backup sample analyzer (hereinafter also referred to as "sub-device") will be described.

When sample analysis is carried out by the first sample analyzer 1, the first sample analyzer 1 is set with the operation mode. The operation mode includes a sampler mode and a manual mode, which are set when the operator operates the input unit 133 of the information processing unit 13.

If the sampler mode is set, the sample rack L holding the sample container T is mounted on the pre-analysis rack holder 121 of the sample transport unit 12 by the operator. The sample rack L mounted on the pre-analysis rack holder 121 is automatically transported by the sample transport unit 12 and transferred on the rack transporting portion 123. During this time, the rack ID is read from the rack barcode of the sample rack L by the barcode reading section 12a, and stored in the RAM 31c of the information processing unit 13 as the rack ID of the sample rack L, in which the sample container being subjected to sample analysis is held, at this time point.

The sample rack is taken into the measurement unit 11 by the sample container take-in portion 11a from the sample rack L in the rack transporting portion 123. In this case, the information of the holding position of the sample rack L from which the sample container T is taken out is stored in the RAM 31c of the information processing unit 13 as the holding position where the sample container, on which the sample analysis is being carried out at the relevant time point, is held. That is, the information of the rack ID and the holding position on the sample to be performed with sample analysis at the relevant time point are stored in the RAM 31c. The barcode reading section 11c reads the sample ID from the sample barcode of the sample container T in the measurement unit 11. The CPU 31a of the information processing unit 13 acquires order information corresponding to the sample ID from a job list registered in advance in the hard disc 31d or the host computer connected through the communication network.

After the order information is acquired, the sample is aspirated from the sample container T, and the sample measurement of the item specified in the order information is carried out by the measurement unit 11. The sample container T in which the aspiration of the sample is completed is discharged from the measurement unit 11 and returned to the original holding position of the sample rack L. In the sample measurement, the reagent and the sample are mixed to prepare the measurement specimen, and the measurement specimen is optically or electrically measured. The measurement data (raw data) obtained by the measurement is provided to the information processing unit 13, so that the CPU 31a of the information processing unit 13 performs an analysis processing to obtain the analysis result. The obtained analysis result is displayed on the image display unit 132.

Such sample measurement is carried out for all the sample containers T of the sample rack L. After the last sample container T is returned to the sample rack L, the sample rack L is transferred from the rack transporting portion 123 to the post-analysis rack holding portion 122. Such operation is carried out on all the sample racks L mounted in the pre-analysis rack holding portion 121.

If the manual mode is set, the operator pushes a take-in button (button switch arranged on the front surface of the measurement unit 11) that instructs the take-in of the sample container T. The sample container take-in portion 11*a* thereby moves forward from the take-in port. The operator installs the sample container T on the installing portion 11*b*, and turns ON a measurement start switch arranged on the front surface of the measurement unit 11. The sample container T is thereby taken into the measurement unit 11.

After the sample container T is taken inside the measurement unit 11, the sample ID is read, the order information is acquired, the sample is aspirated, and the sample is measured, similar to the sampler mode. The sample container T from which the sample is aspirated is discharged to outside the measurement unit 11 when the sample container take-in portion 11*a* moves forward from the take-in port. The operator removes the sample container T from the sample container take-in portion 11*a*, installs the sample container T accommodating the sample to be measured next in the sample container take-in portion 11*a*, and turns ON the measurement start switch. The next sample container T is thereby taken into the measurement unit 11, and the sample measurement is carried out.

Figure 9:
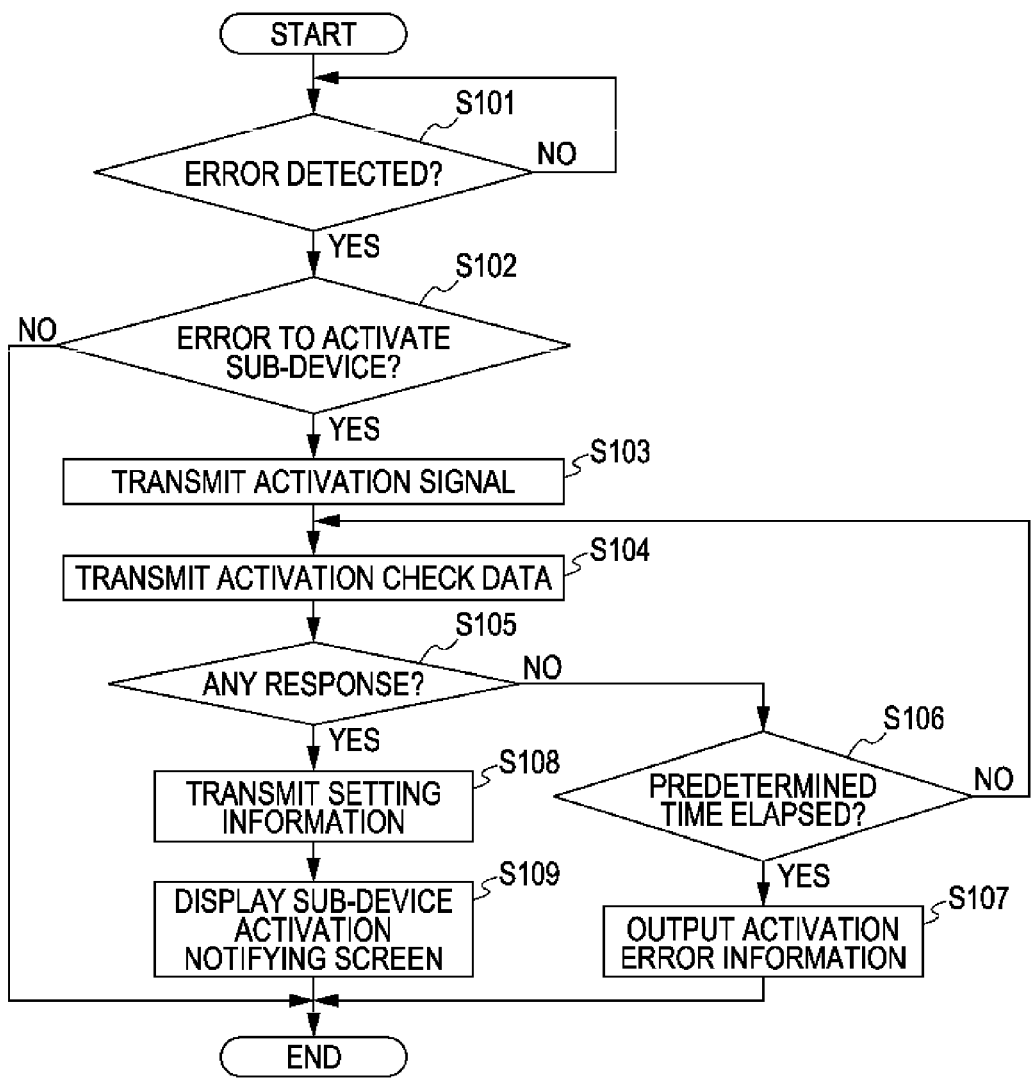
FIG. 9 is a flowchart showing a procedure of an operation of the information processing unit of the first sample analyzer according to the first embodiment.

The information processing unit 13 of the first sample analyzer 1 monitors the occurrence of abnormality of the first sample analyzer 1. FIG. 9 is a flowchart showing a procedure of an operation of the information processing unit 13 of the first sample analyzer 1 in this case. The monitoring of the occurrence of abnormality of the first sample analyzer 1 is carried out by having the CPU 31*a* monitor the output signals of the ammeter 112, the water leakage sensor 113, the pressure sensor 114, and the liquid amount sensor 118. The CPU 31*a* determines whether or not error is detected (step S101), and again executes the processing of step S101 if the error is not detected (NO in step S101).

If the error is detected in step S101 (YES in step S101), the CPU 31*a* references the first abnormality database DB1 and the second abnormality database DB2, and determines whether or not the detected abnormality is the abnormality for activating the second sample analyzer 2, which is the sub-device (step S102). If the detected abnormality is not the abnormality for activating the sub-device (NO in step S102), the CPU 31*a* terminates the processing.

If the detected abnormality is the abnormality for activating the sub-device (YES in step S102), the CPU 31*a* transmits an activation signal for activating the sub-device to the wireless communication unit 14 (step S103). Thereafter, the CPU 31*a* causes the wireless communication unit 14 to transmit activation check data for checking that activation has been performed to the second sample analyzer 2, which is the sub-device (step S104). After the transmission of the activation check data, the CPU 31*a* determines whether or not response data is received from the second sample analyzer 2 (step S105), and determines whether or not a predetermined time has elapsed from the transmission of the activation signal (step S106) if the response data is not received (NO in step S105). If the predetermined time has not elapsed from the transmission of the activation signal in step S106 (NO in step S106), the CPU 31*a* returns the processing to step S104 and causes the wireless communication unit 14 to transmit the activation check data again.

Figure 10:
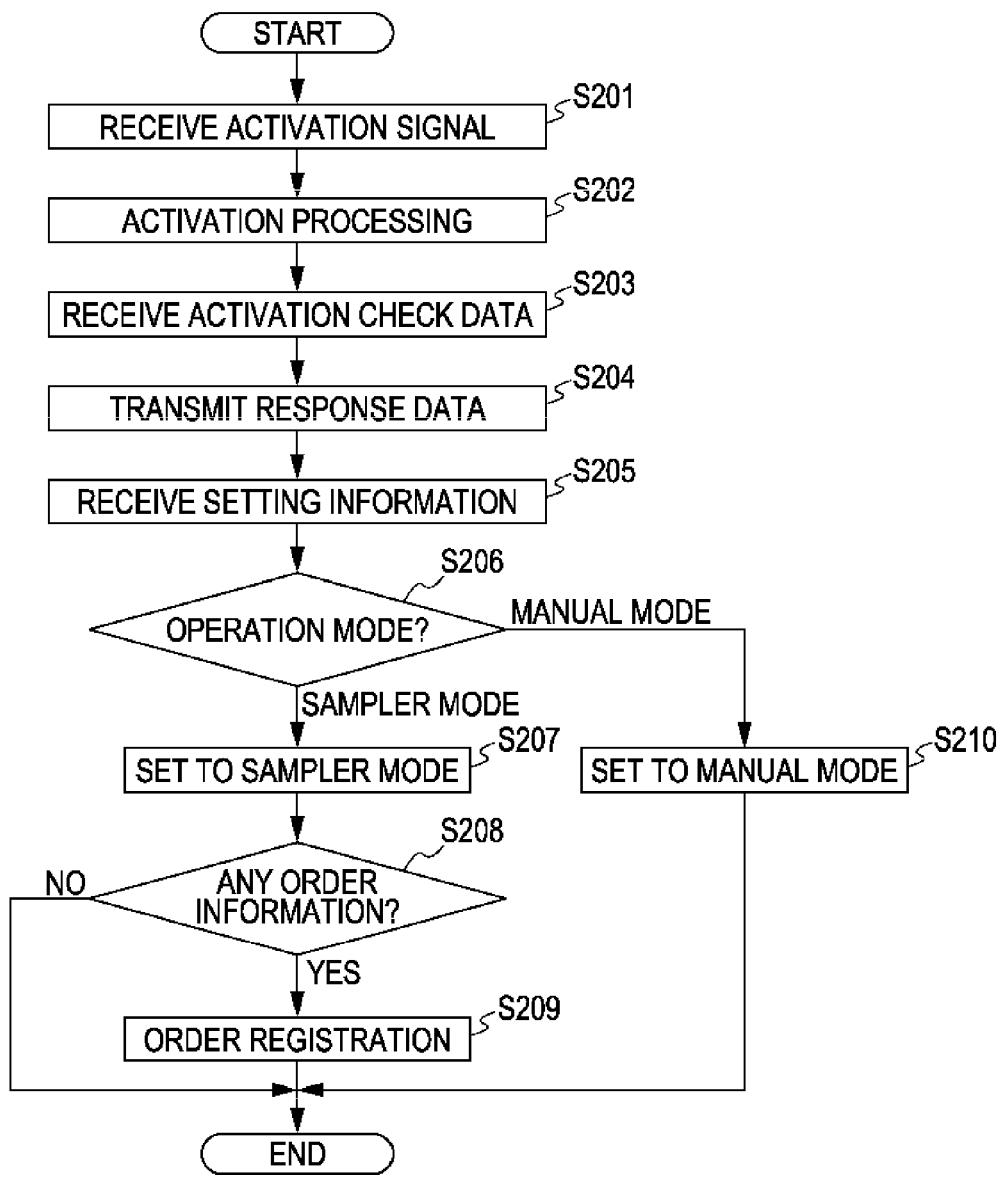
FIG. 10 is a flowchart showing a procedure of an operation of the information processing unit of the second sample analyzer according to the first embodiment.

The operation of the second sample analyzer 2, which is the sub-device, will now be described. FIG. 10 is a flowchart showing a procedure of an operation of the information processing unit 23 of the second sample analyzer 2. When the wireless communication unit 24 receives the activation signal (step S201), the activation processing is executed by the CPU 41*a* through the input/output interface 41*f* (step S202). The measurement unit 21, the sample transport unit 22, and the information processing unit 23 are activated by the activation processing. After the activation processing is finished, the activation check data is received by the wireless communication unit 24 and provided to the CPU 41*a* (step S203). When receiving the activation check data, the CPU 41*a* transmits response data, which is ACK signal with respect to the activation check data, to the wireless communication unit 24 (step S204).

The description now returns to the operation of the first sample analyzer 1, which is the main device. When the wireless communication unit 24 receives the response data from the sub-device, the response data is provided to the CPU 31*a* (YES in step S105). In this case, the CPU 31*a* transmits the setting information used in the setting of the sub-device to the wireless communication unit 14 (step S108).

The setting information includes a case in which the setting information instructing mode setting and setting information instructing order registration are included, and a case in which only the setting information instructing mode setting is included. FIG. 11 is a view describing the setting information. The setting information instructing the mode setting (hereinafter referred to as "mode setting information") starts from a mode setting instructing identifier "SU"). A data-delimiter "¥" follows after the mode setting instructing identifier, and then the mode information follows thereto. The mode information is information indicating the mode to set to the sub-device, and is "Sampler" in the case of sampler mode and "Manual" in the case of manual mode.

If the mode setting information is information instructing the setting of the sampler mode to the sub-device, the setting information includes setting information instructing order registration (hereinafter referred to as "order registration information"). The order registration information starts from an order registration instructing identifier "JR". A data-delimiter "¥" follows after the order registration instructing identifier, and then each information of rack ID, position of sample container, sample ID, patient ID, measurement item, order presence/absence follows thereto. The data-delimiter "¥" is inserted between the information. In the example of the order registration information shown in FIG. 11, the rack ID is "10001", the position of the sample container is "01", the sample ID is "20111124 101 Sampler 001", the patient ID is "Patient ID 000001", the measurement item is "WBC", the order presence/absence thereof is "1", the next measurement item is "HGB", the order presence/absence thereof is "1", the next measurement item is "HCT", and the order presence/absence thereof is "0".

The order registration information includes order information on all the samples held in the sample rack L on the rack transporting portion 123 at the time point the error occurred (i.e., time point of executing step S108). That is, as described above, if the first sample analyzer 1 is operating in the sampler mode, the RAM 31*c* of the information processing unit 13 stores the rack ID of the sample rack L on the rack transporting portion 123 at the relevant time point. If error occurs in the first sample analyzer 1 in a state the sampler mode is set, the CPU 31*a* generates the setting information including the mode setting information instructing the setting of the sampler mode to the sub-device and the order registration information including the order information of the sample rack L in the middle of the sample measurement at the relevant time point. More specifically, the CPU 31*a* reads out the order information including the rack ID from the hard disc 31*d* of the information processing unit 31 with the rack ID stored in the RAM 31*c* at the relevant time point as the key, and generates the order registration information from the sample ID, the patient ID, and the measurement item in which measurement is specified contained in the order information.

If error occurs in a state the first sample analyzer 1 is set to the manual mode, the CPU 31*a* generates the setting information including only the mode setting information instructing the setting of the manual mode to the sub-device.

After the setting information generated in such manner is transmitted by the wireless communication unit 14, the CPU 31*a* displays a sub-device activation notifying screen for notifying the operator that the activation of the sub-device is completed on the image display unit 132 (step S109), and terminates the processing.

If a predetermined time has elapsed from the transmission of the activation signal without receiving the response data from the sub-device (NO in step S106), the CPU 31*a* displays activation error information notifying that the activation of the sub-device failed on the image display unit 132 (step S107), and terminates the processing. The operator thus can recognize that the activation of the second sample analyzer 2, which is the sub-device, failed by checking the activation error information without moving close to the second sample analyzer 2 to check.

The operation of the second sample analyzer 2, which is the sub-device, will now be described. After transmitting the response data with respect to the activation check data to the wireless communication unit 24, the setting information is transmitted from the first sample analyzer 1. The setting information is received by the wireless communication unit 24 and provided to the CPU 41*a* (step S205). The CPU 41*a* determines which operation mode, the sampler mode or the manual mode, is instructed to be set in the setting information (step S206). If the setting of the sampler mode is instructed ("sampler mode" in step S206), the CPU 41*a* sets the operation mode to the sampler mode (step S207). In this case, the CPU 41*a* determines whether or not the setting information includes the order registration instructing information (step S208), registers the order information in the hard disc 41*d* according to the order registration instructing information (step S209) if the setting information includes the order registration instructing information (YES in step S208), and terminates the processing. If the setting information does not include the order registration instructing information (NO in step S208), the CPU 41*a* terminates the processing as it is.

If the setting of the manual mode is instructed in the setting information ("manual mode" in step S206), the CPU 41*a* sets the operation mode to the manual mode (step S210) and terminates the processing.

The sub-device activation notifying screen will be described below. In step S109, the information to display changes according to the operation setting state of the first sample analyzer 1 at the time point error occurred. FIG. 12 is a view showing one example of a sub-device activation notifying screen. At the time point error occurred in the first sample analyzer 1, when the sampler mode is set and the sample rack L is being automatically transported by the sample transport unit 12, information notifying to move the sample rack L on the rack transporting portion 123 to the sub-device is displayed. In the sub-device activation notifying screen D1, the rack ID of the sample rack L on the rack transporting portion 123 is shown, and a message notifying to move the sample rack L to the sub-device is shown. Furthermore, in the sub-device activation notifying screen D1, a message notifying to move the sample rack L in which measurement is not yet performed, that is, the sample rack L held in the pre-analysis rack holding portion 121 to the sub-device is shown. Furthermore, graphic information G1, which is an illustration, showing to move the sample rack L from the main device to the sub-device, is displayed with such messages. The sub-device activation notifying screen D1 is created using the rack ID stored in the RAM 31*c*. In such sub-device activation notifying screen D1, an OK button C1, which is a button control, is displayed, so that the sub-device activation notifying screen D1 is closed when the operator selects the OK button C1 with the click operation of the mouse, and the like.

In addition, the sub-device activation notifying screen including a message indicating that the sub-device is activated is displayed if error occurred in the first sample analyzer 1 operating in the manual mode.

When the second sample analyzer 2, which is the sub-device, is activated, the operator uses the second sample analyzer 2 to continue the sample analysis. While performing the sample analysis in the second sample analyzer 2, the operator or the service man can perform the recovery work of the first sample analyzer.

After the first sample analyzer 1 is recovered, the sample analysis can be carried out again by the first sample analyzer 1. In this case, the second sample analyzer 2 for backup is again returned to the shutdown state. In the sample analyzing system 100 according to the present embodiment, the second sample analyzer 2 can be remotely shut down from the first sample analyzer 1 in this case. The remote shutdown operation will be described below.

Figure 13:
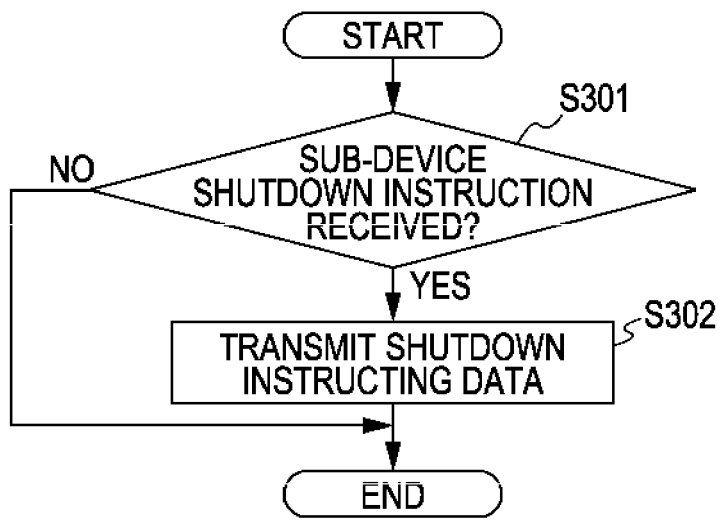
FIG. 13 is a flowchart showing a procedure of an operation of the information processing unit of the first sample analyzer in the remote shutdown operation.
Figure 14:
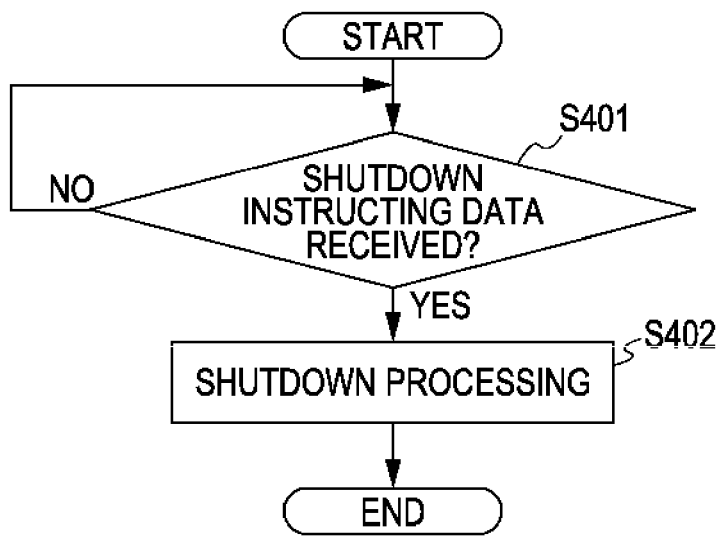
FIG. 14 is a flowchart showing a procedure of an operation of the information processing unit of the second sample analyzer in the remote shutdown operation.

FIG. 13 is a flowchart showing a procedure of the operation of the information processing unit 13 of the first sample analyzer 1 in the remote shutdown operation, and FIG. 14 is a flowchart showing a procedure of an operation of the information processing unit 23 of the second sample analyzer 2 in the remote shutdown operation. In the information processing unit 13, a screen for remotely instructing the shutdown of the sub-device can be displayed. In this screen, the operator can instruct the shutdown of the sub-device. After the recovery work of the first sample analyzer 1 is finished, the operator operates the input unit 133 of the information processing unit 13 to instruct remote shutdown of the sub-device. The CPU 31*a* determines whether or not the shutdown instruction of the sub-device is received (step S301), causes the wireless communication unit 14 to transmit the shutdown instructing data instructing the shutdown (step S302) when receiving the shutdown instruction of the sub-device (YES in step S301), and terminates the processing. If the shutdown instruction of the sub-device is not received (NO in step S301), the CPU 41*a* terminates the processing as it is.

The CPU 41*a* of the second sample analyzer 2, which is the sub-device, determines whether or not the shutdown instructing data is received by the wireless communication unit 24 (step S401). If the shutdown instructing data is not received by the wireless communication unit 24 (NO in step S401), the CPU 41*a* again executes the processing of step S401. The CPU 41*a* waits for the reception of the shutdown instructing data by repeating the above processing.

If the shutdown instructing data is received by the wireless communication unit 24, the shutdown instructing data is provided to the CPU 41*a*. In this case (YES in step S401), the CPU 41a executes the shutdown processing of the second sample analyzer 2 (step S402), and terminates the processing.

According to the above configuration, when a trouble such as a specific abnormality occurs in the first sample analyzer, which is the main device, the second sample analyzer, which is the sub-device, is automatically activated so that the second sample analyzer can be rapidly activated compared to the prior art. Furthermore, the second sample analyzer is automatically activated and the sample processing can be suppressed from stagnating even when the operator does not notice the occurrence of abnormality in the first sample analyzer or when a great amount of time is required in the determination on whether or not the abnormality that takes time to recover.

Since the first sample analyzer 1 transmits the setting information based on the operation setting at the time point of occurrence of error, and the second sample analyzer 2 performs the operation setting of the second sample analyzer 2 according to the setting information received by the second sample analyzer 2, the activated second sample analyzer can be set to a state preferred at the relevant time point. For example, the operation mode of the second sample analyzer is instructed to be set to the sampler mode in the setting information when the first sample analyzer 1 is operating in the sampler mode, and the operation mode of the second sample analyze is instructed to be set to the manual mode in the setting information when the first sample analyzer 1 is operating in the manual mode. Thus, the operator can use the second sample analyzer 2 similar to the first sample analyzer 1 before the occurrence of error.

When the first sample analyzer 1 is operating in the sampler mode, the order information of the sample held in the sample rack L being transported to the rack transporting portion 123 is transmitted to the second sample analyzer 2 by the setting information, and the second sample analyzer 2 registers the order according to the received setting information. The operator then can analyze the sample of the sample rack L being transported without registering the order information in the second sample analyzer 2 by moving the sample rack L on the rack transporting portion 123 of the first sample analyzer 1 to the second sample analyzer 2.

Furthermore, since the sub-device activation notifying screen is displayed on the image display unit 132 of the first sample analyzer 1, the operator can easily recognize which sample rack L to move to the second sample analyzer 2 by checking the screen.

Second Embodiment

Configuration of Sample Analyzing System

Figure 15:
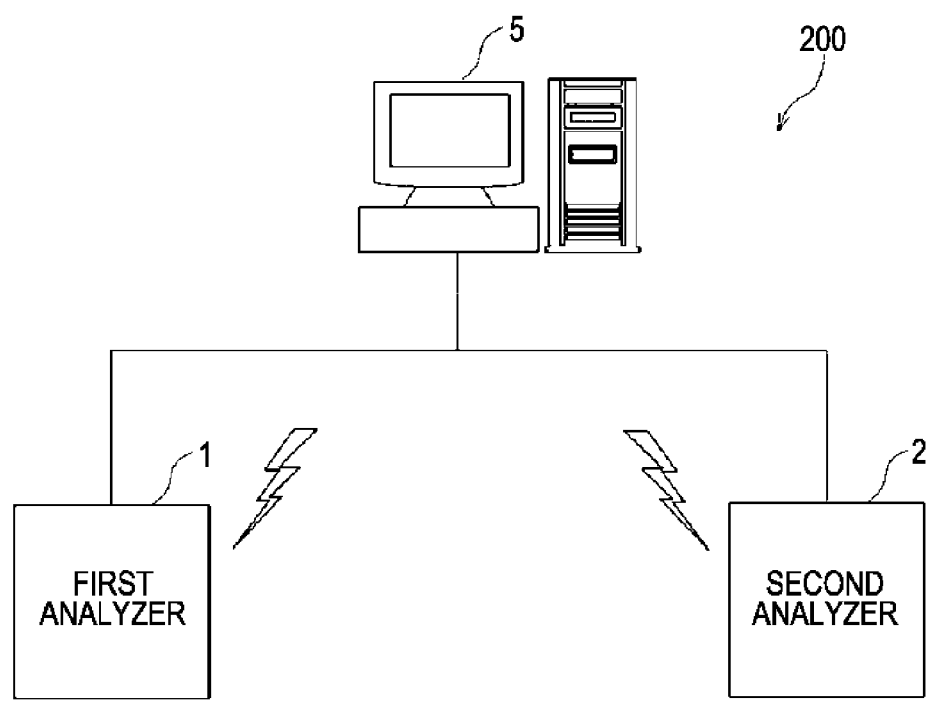
FIG. 15 is a schematic view showing an overall configuration of a sample analyzing system according to a second embodiment.

FIG. 15 is a schematic view showing an overall configuration of a sample analyzing system according to the present embodiment. A sample analyzing system 200 according to the present embodiment includes a first sample analyzer 1, a second sample analyzer 2, and a test information management device 5. The first sample analyzer 1 includes the wireless communication unit 14, and the second sample analyzer 2 includes the wireless communication unit 24. The configurations of the first sample analyzer 1, the second sample analyzer 2, and the wireless communication units 14, 24 are similar to the configurations described in the first embodiment, and thus the description thereof will be omitted.

Figure 16:
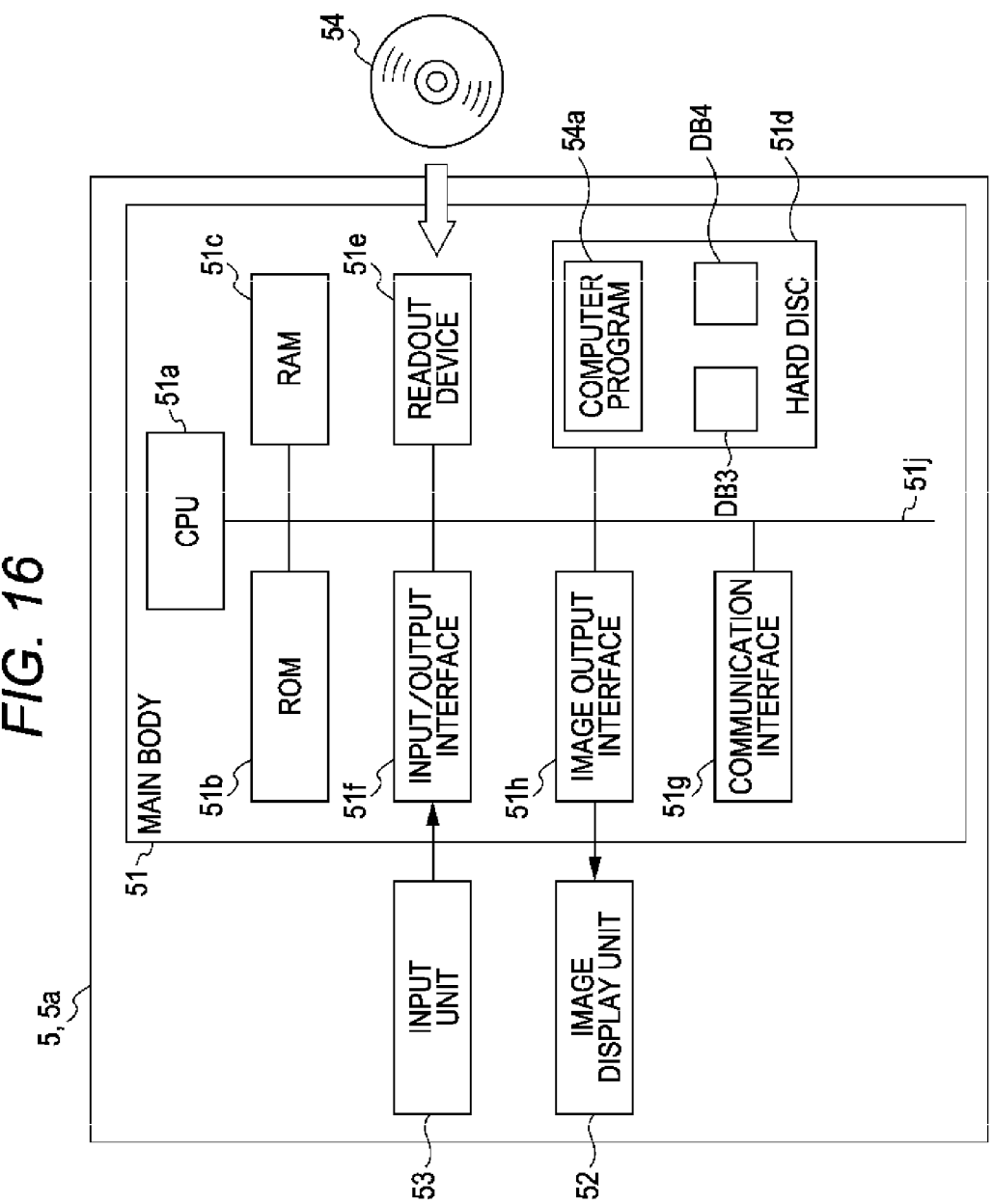
FIG. 16 is a block diagram showing a configuration of a test information management device.

The test information management device 5 is a device for managing the test information (order information, sample analysis result, etc.) of the first sample analyzer 1 and the second sample analyzer 2. FIG. 16 is a block diagram showing a configuration of the test information management device 5. The test information management device 5 is configured by a computer. As shown in FIG. 16, a computer 5a includes a main body 51, an image display unit 52, and an input unit 53. The main body 51 includes a CPU 51a, a ROM 51b, a RAM 51c, a hard disc 51d, a readout device 51e, an input/output interface 51f, a communication interface 51g, and an image output interface 51h, where the CPU 51a, the ROM 51b, the RAM 51c, the hard disc 51d, the readout device 51e, the input/output interface 51f, the communication interface 51g, and the image output interface 51h are connected by a bus 51j.

The communication interface 51g is Ethernet (registered trademark) interface. The communication interface 51g is connected to the first sample analyzer 1 and the second sample analyzer 2 through the LAN. The computer 5a can transmit and receive data with the first sample analyzer 1 and the second sample analyzer 2 connected to the LAN using a predetermined communication protocol by the communication interface 51g.

The hard disc 51d includes an order information database DB3 and an analysis result database DB4. The order information input from the operator is registered in the order information database DB3. The analysis results of the first sample analyzer 1 and the second sample analyzer 2 are stored in the analysis result database DB4.

Other configurations of the test information management device 5 are similar to the configurations of the information processing unit 13 described in the first embodiment, and thus the description thereof will be omitted.

Configuration of Sample Analyzing System

The test information management device 5 can register the order information by the input from the operator. When reading the sample ID from the sample container T, the first sample analyzer 1 or the second sample analyzer 2 makes an order inquiry to the test information management device 5 with the relevant sample ID as a key. The test information management device 5 searches the order information that matches the sample ID in the database DB3 in response to the order inquiry, and transmits the searched order information to the sample analyzer that made the inquiry. The order information is provided to the sample analyzer in such manner.

The first sample analyzer 1 or the second sample analyzer 2 performs the sample analysis according to the acquired order information, and transmits the sample analysis result to the test information management device 5. When receiving the sample analysis result, the test information management device 5 registers the received sample analysis result in the analysis result database DB4.

A case in which the first sample analyzer 1 is the main device and the second sample analyzer 2 is the sub-device will be hereinafter described.

Figure 17:
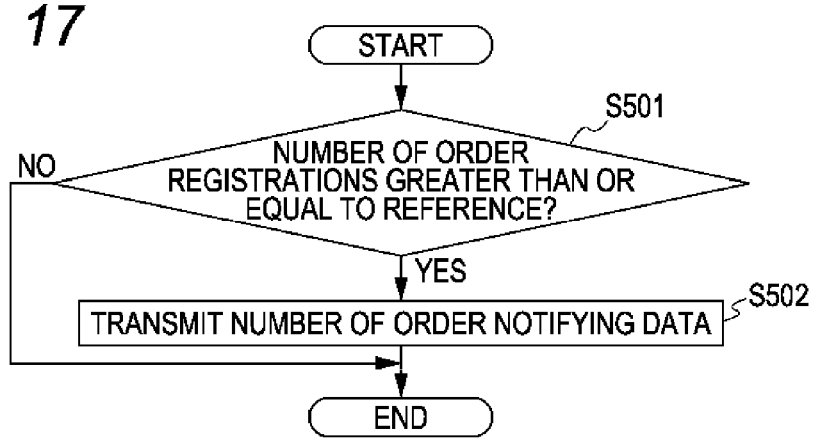
FIG. 17 is a flowchart showing a procedure of an operation of the test information management device according to the second embodiment.

FIG. 17 is a flowchart showing a procedure of an operation of the test information management device 5 according to the present embodiment. In this case, the order information is transmitted only to the first sample analyzer 1, which is the main device, from the test information management device 5. The CPU 51a of the test information management device 5 calculates the number of order information (hereinafter referred to as "number of order registration") registered in the order information database DB3, and determines whether or not the number of order registrations is greater than or equal to a predetermined reference value (step S501). If the number of order registrations is greater than or equal to the reference value (YES in step S501), the CPU 51a transmits number of order notifying data indicating the number of order registrations to the first sample analyzer 1, which is the main device (step S502), and terminates the processing. If the number of order registration is smaller than the reference value (NO in step S501), the CPU 51*a* terminates the processing as it is.

Figure 18:
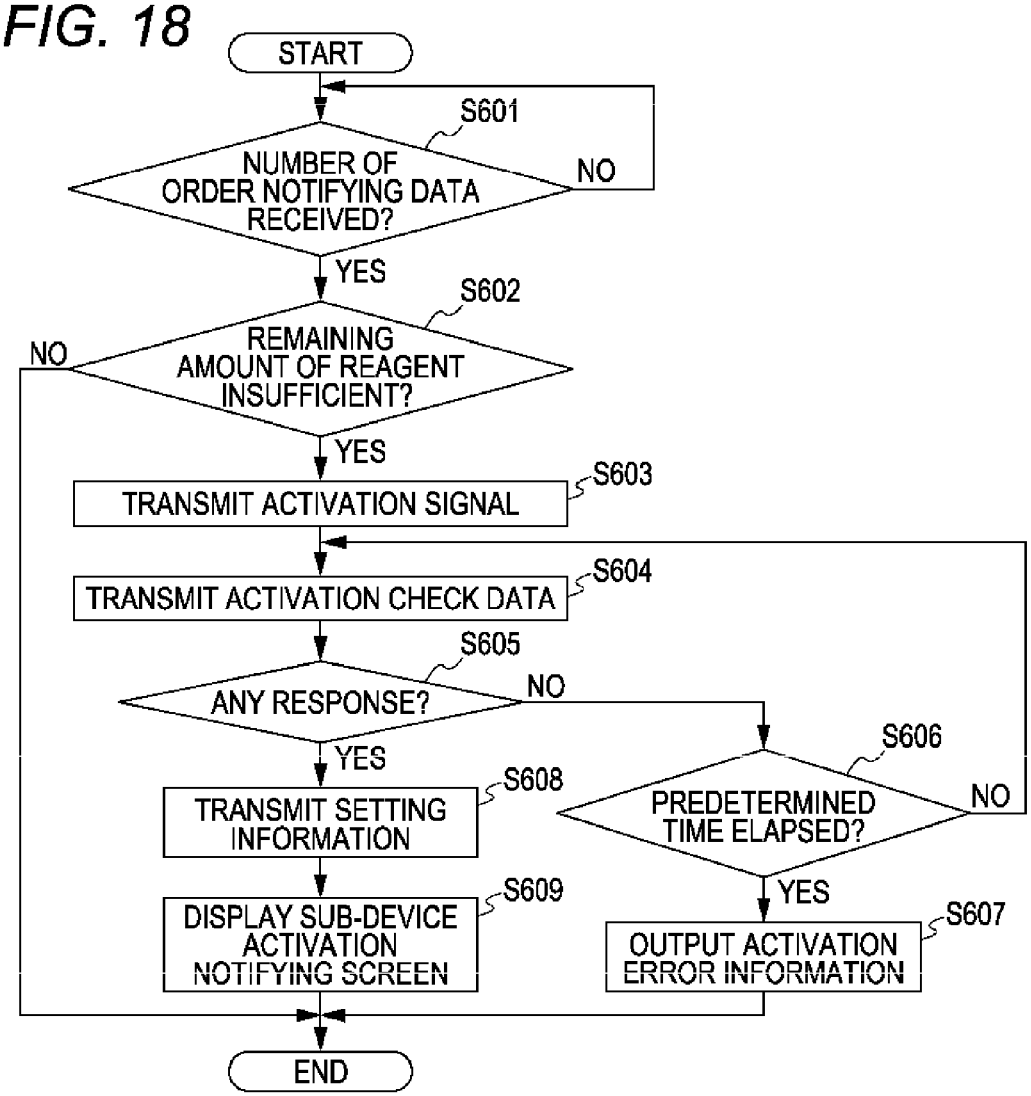
FIG. 18 is a flowchart showing a procedure of an operation of the information processing unit of the first sample analyzer according to the second embodiment.

FIG. 18 is a flowchart showing a procedure of an operation of the information processing unit 13 of the first sample analyzer 1 according to the present embodiment. The CPU 31*a* of the first sample analyzer 1, which is the main device, determines whether or not the number of order notifying data transmitted from the test information management device is received (step S601). If the information processing unit 13 has not received the number of order notifying data (NO in step S601), the CPU 31*a* again executes the processing of step S601. The CPU 31*a* waits for the reception of the number of order notifying data by repeating the above processing.

If the number of order notifying data is received by the information processing unit 13, such number of order notifying data is provided to the CPU 31*a*. In this case (YES in step S601), the CPU 31*a* references the reagent remaining amount information 34*b*, and determines whether or not the remaining amount of reagent is insufficient for the sample analysis of the number of order registrations (step S602). If not determined that the remaining amount of reagent is insufficient (NO in step S602), the CPU 31*a* terminates the processing as it is.

If determined that the remaining amount of reagent is insufficient (YES in step S602), determination can be made that the number of order registrations is excessively large with only the first sample analyzer 1, and thus the CPU 31*a* transmits an activation signal for activating the sub-device to the wireless communication unit 14 (step S603).

The processing of steps S604 to S609 are similar to the processing of steps S104 to S109 described in the first embodiment, and hence the description thereof will be omitted. In the sub-device activation notifying screen displayed in step S609, the rack ID of the moving sample rack L is not displayed, and a message indicating that the activation of the sub-device is completed, and that the sample rack L holding the non-measured sample is moved to the sub-device, and the like is displayed.

The operation of the second sample analyzer 2 according to the present embodiment is similar to the operation of the second sample analyzer 2 according to the first embodiment, and thus the description thereof will be omitted.

According to the above configuration, if the number of order registrations is excessively large with respect to the processing ability of the first sample analyzer 1, which is the main device, the second sample analyzer 2, which is the sub-device, is automatically activated, and hence the sub-device is efficiently activated and the sample processing ability of the entire sample analyzing system 200 can be rapidly increased.

Third Embodiment

The second sample analyzer 2 according to the present embodiment has power supplied to the communication interface 41*g* in the shutdown state. In this state, the communication interface 41*g* is able to receive the activation signal, and the power of the information processing unit 23 can be turned ON when the communication interface 41*g* receives the activation signal. The information processing unit 23 is thereby automatically activated. When the information processing unit 23 is activated, the measurement unit 21 and the sample transport unit 22 are also activated accordingly, and the entire second sample analyzer 2 is activated. Other configurations of the sample analyzing system according to the present embodiment are similar to the configurations of the sample analyzing system 200 according to the second embodiment, and hence the same reference numerals are denoted on the same configuring elements and the description thereof will be omitted.

Figure 19:
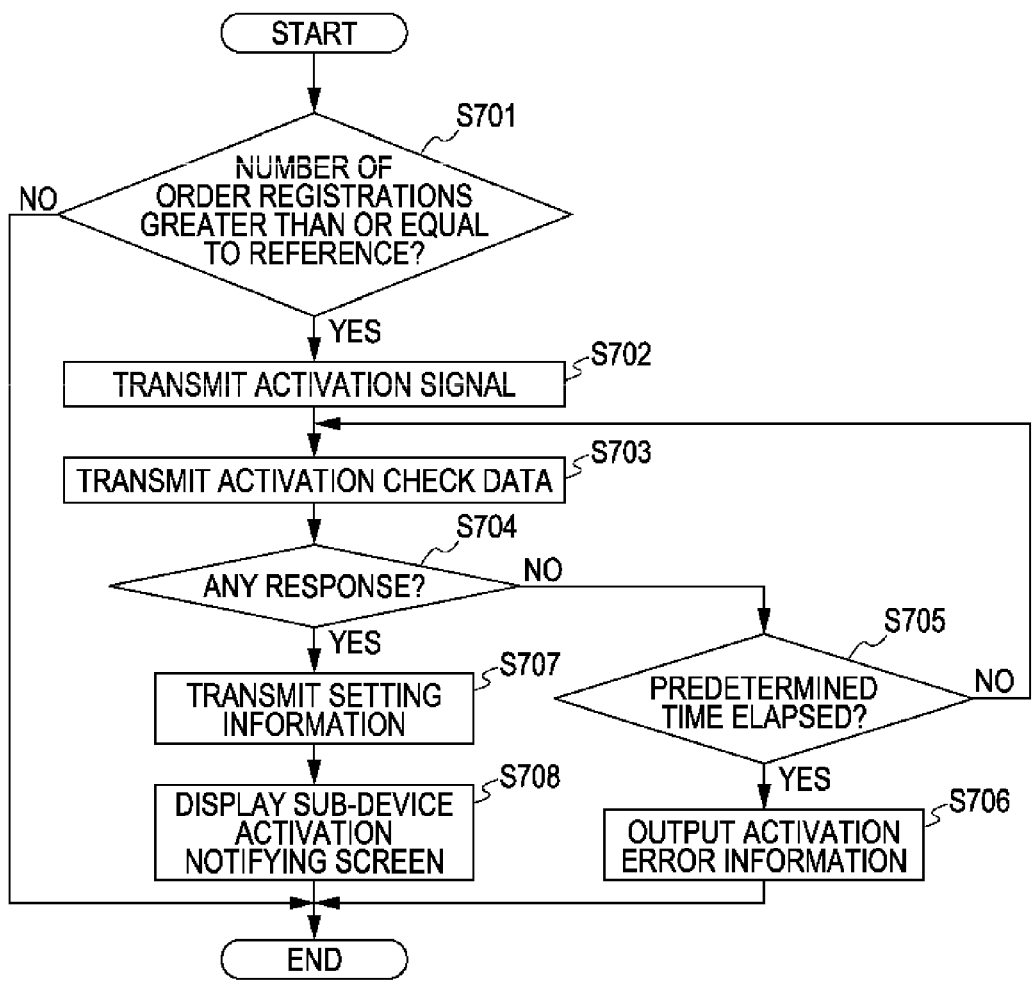
FIG. 19 is a flowchart showing a procedure of an operation of the test information management device according to a third embodiment.

FIG. 19 is a flowchart showing a procedure of an operation of the test information management device 5 according to the present embodiment. In this case, the order information is transmitted only to the first sample analyzer 1, which is the main device, from the test information management device 5. The CPU 51*a* of the test information management device 5 calculates the number of order registration in the order information database DB3, and determines whether or not the number of order registrations is greater than or equal to a predetermined reference value (step S701). If the number of order registration is smaller than the reference value (NO in step S701), the CPU 51*a* terminates the processing as it is. If the number of order registrations is greater than or equal to the reference value (YES in step S701), the CPU 51*a* causes the communication interface 51*g* to transmit the activation signal for activating the sub-device (step S702).

The processing of steps S703 to S708 are processing executed by the CPU 51*a* of the test information management device 5 but are similar to the processing of steps S104 to S109 described in the first embodiment, and hence the description thereof will be omitted. The activation check data is transmitted by the communication interface 51*g* in step S703, and the response data is received by the communication interface 51*g* in step S705. In step S707, the CPU 51*a* causes the communication interface 51*g* to transmit predetermined setting information. Further, in step S708, the sub-device activation notifying screen is displayed on the image display unit 52 of the test information management device 5, and in step S706, the activation error information is displayed on the image display unit 52. In the sub-device activation notifying screen displayed in step S708, the rack ID of the moving sample rack L is not displayed, and a message indicating that the activation of the sub-device is completed, and that the sample rack L holding the non-measured sample is moved to the sub-device, and the like is displayed.

The operation of the second sample analyzer 2 according to the present embodiment is substantially the same as the operation of the second sample analyzer 2 according to the first embodiment, and thus the description thereof will be omitted. The activation signal is received by the communication interface 41*g* in step S201, the activation check data is received by the communication interface 41*g* in step S203, the response data is transmitted by the communication interface 41*g* in step S204, and the setting information is received by the communication interface 41*g* in step S205.

According to the above configuration, if the number of order registrations is excessively large with respect to the processing ability of the first sample analyzer 1, which is the main device, that is, if a trouble in that the sample processing ability is insufficient with only the first sample analyzer 1, which is the main device, occurs, the second sample analyzer 2, which is the sub-device, is automatically activated, and hence the sub-device is efficiently activated and the sample processing ability of the entire sample analyzing system 200 can be rapidly increased.

Fourth Embodiment

The configuration of the sample analyzing system according to the present embodiment is similar to the configurations of the sample analyzing system 100 according to the first embodiment, and hence the same reference numerals are denoted on the same configuring elements and the description thereof will be omitted.

In the present embodiment, one day is divided into two periods, from 0 o'clock to 12 o'clock and from 12 o'clock to 24 o'clock, where the sample analysis is performed by the first sample analyzer 1 in one period and the sample analysis is performed by the second analyzer 2 in the other period.

Figure 20:
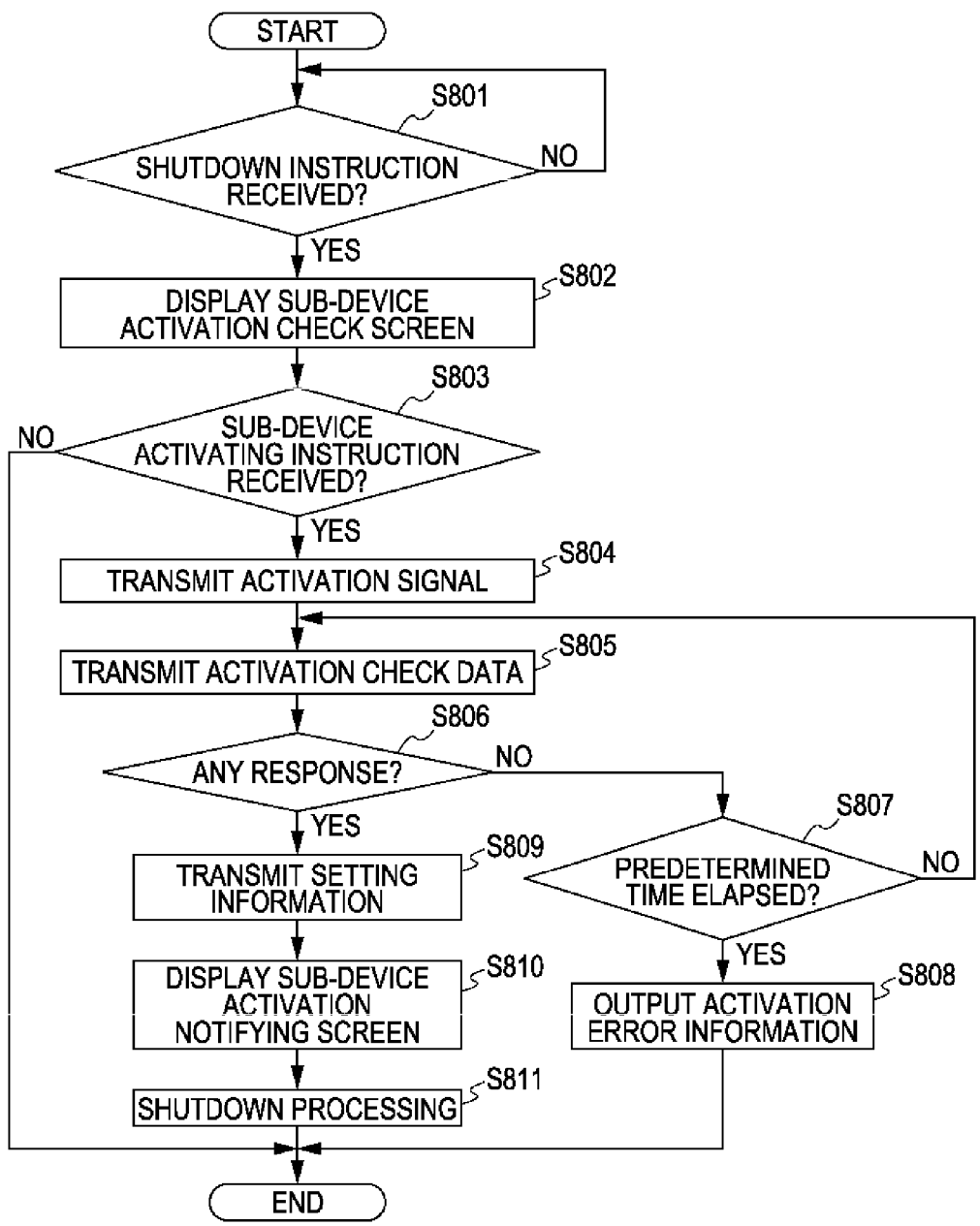
FIG. 20 is a flowchart showing a procedure of an operation of the information processing unit of the first sample analyzer according to a fourth embodiment.

FIG. 20 is a flowchart showing a procedure of an operation of the information processing unit 13 of the first sample analyzer 1 according to the present embodiment. When performing the sample analysis with the first sample analyzer 1, the operator checks whether the switching time to the second sample analyzer 2 is reached, operates the input unit 133 if the switching time is reached, and gives the shutdown instruction of the first sample analyzer 1 to the information processing unit 13. The CPU 31*a* determines whether or not the shutdown instruction is received (step S801). If the shutdown instruction is not received (NO in step S801), the CPU 31*a* again executes the processing of step S301. The CPU 31*a* waits for the instruction of shutdown by repeating the above processing.

Figure 21:
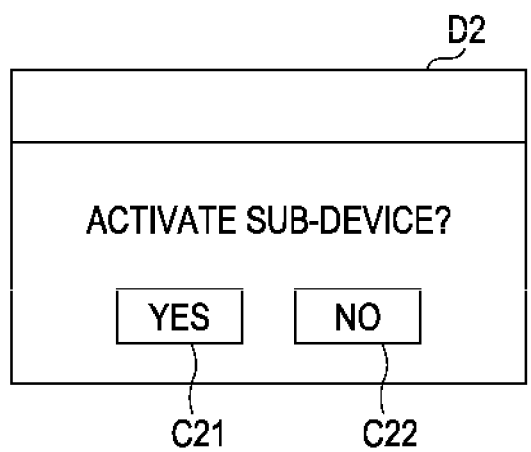
FIG. 21 is a view showing a sub-device activation check screen.

If the instruction of shutdown is received (YES in step S801), the CPU 31*a* displays the sub-device activation check screen for checking the activation of the sub-device on the image display unit 132 (step S802). FIG. 21 is a view showing a sub-device activation check screen. As shown in FIG. 21, the sub-device activation check screen D2 includes a character string "activate sub-device?". The sub-device activation check screen D2 includes a button C21 for instructing the activation of the sub-device and a button C22 for not instructing the activation of the sub-device. The operator can select either buttons C21 or C22 by the clicking operation of the mouse.

After displaying the sub-device activation check screen D2, the CPU 31*a* determines whether or not the instruction to activate the sub-device is received (step S803). If the operator selects the button C22 and the CPU 31*a* does not receive the instruction to activate the sub-device (NO in step S803), the CPU 31*a* terminates the processing as it is. If the operator selects the button C21 and the CPU 31*a* receives the instruction to activate the sub-device (YES in step S803), the CPU 31*a* causes the wireless communication unit 14 to transmit the activation signal for activating the sub-device (step S804).

The processing of steps S804 to S810 are similar to the processing of steps S104 to S109 described in the first embodiment, and hence the description thereof will be omitted.

After displaying the sub-device activation notifying screen in step S810, the CPU 31*a* executes the shutdown processing of the first sample analyzer 1 (step S811), and terminates the processing.

The operation of the second sample analyzer 2 according to the present embodiment is similar to the operation of the second sample analyzer 2 according to the first embodiment, and thus the description thereof will be omitted.

According to the above configuration, when switching from the use of the first sample analyzer 1, which is the main device, to the use of the second sample analyzer 2, which is the sub-device, the second sample analyzer 2 is automatically activated when the operator instructs the shutdown of the first sample analyzer 1 and instructs the activation of the second sample analyzer, and thus the second sample analyzer 2 is efficiently activated and the switching work can be efficiently carried out.

Other Embodiments

In the first embodiment described above, the configuration in which the second sample analyzer 2 is set to the sampler mode if error occurs in the first sample analyzer 1 operating in the sampler mode, and the second sample analyzer 2 is set to the manual mode if error occurs in the first sample analyzer 1 operating in the manual mode, but this is not the sole case. When error occurs in the first sample analyzer 1 operating in the sampler mode, the setting information including the setting instructing information of the manual mode may be transmitted to the second sample analyzer 2 to set the second sample analyzer 2 to the manual mode. When the first sample analyzer 1 is operating in the sampler mode, the sample is automatically aspirated from the sample container held in the sample rack L, but in this case, error occurs after the sample is aspirated and before the sample measurement is completed, and hence the sample enough to perform the sample measurement on all the items specified in the order information may not be left in the sample container T if the sample measurement is not completed. In such a case, the order information needs to be reregistered manually to perform the manual measurement, and thus the relevant sample can be efficiently measured by setting the second sample analyzer 2 to the manual mode.

In the first embodiment described above, whether or not to use for the activation of the second sample analyzer 2 can be set by the user for each abnormality in the second abnormality database DB2, but this is not the sole case. For example, the second sample analyzer 2 may be activated when the abnormality registered in the first abnormality database DB1 occurs and the second sample analyzer 2 may not be activated when the abnormality registered in the second abnormality database DB2 occurs, in which case the second abnormality database DB2 cannot be setting changed by the user.

In the first to fourth embodiments described above, a configuration in which the first sample analyzer 1 includes one measurement unit 11 has been described, but this is not the sole case. The sample analyzer may be configured by two or more measurement units and one information processing unit. The measurement unit and the information processing unit may not be separately arranged, and a sample analyzer in which the function corresponding to the measurement unit and the function corresponding to the information processing unit are provided in one housing may be obtained. This is the same for the second sample analyzer 2.

In the first to fourth embodiments described above, the configuration in which the measurement unit 11 does not include a calculation unit such as the CPU, and the like, and the operation control of the measurement unit 11 is carried out by the CPU 31*a* of the information processing unit 13 has been described, but this is not the sole case. A configuration in which the measurement unit includes a control unit including a CPU, a memory, and the like, and the operation control of the measurement mechanism is carried out by the control unit may be adopted. This is the same for the second sample analyzer 2.

In the first to fourth embodiments described above, a configuration in which the second sample analyzer 2 is activated when the first sample analyzer 1 transmits the activation signal by the wireless communication unit 14, and the activation signal is received by the wireless communication unit 24 has been described, but this is not the sole case. A configuration in which the first sample analyzer 1 and the second sample analyzer 2 can be communicated by a wired LAN, and the second sample analyzer 2 is activated when the activation signal is transmitted from the communication interface 31*g* of the first sample analyzer 1 and the activation signal is received by the communication interface 41*g* of the second sample analyzer 2 may be adopted.

In the first to fourth embodiments described above, the configuration in which a state where power is not supplied to the measurement unit 21, the sample transport unit 22, and the information processing unit 23 but a state where power is supplied to the input/output interface 41f and the wireless communication unit 24 is the shutdown state of the second sample analyzer 2 has been described, but this is not the sole case. A configuration in which a state where power is not supplied to the measurement unit 21 and the sample transport unit 22 but power is supplied to the information processing unit 23, the input/output interface 41f, and the wireless communication unit 24, and the operating system of the information processing unit 23 is activated but the application program for controlling the second sample analyzer 2 is not activated is the shutdown state of the second sample analyzer 2 may be adopted.

In the first to fourth embodiments described above, an example of configuring the first sample analyzer 1 and the second sample analyzer 2 by the multi-item blood cell analyzer for detecting the blood cells contained in the blood sample as white blood cells, red blood cells, blood platelets, and the like and counting each blood cell has been described, but this is not the sole case. For example, the first sample analyzer 1 and the second sample analyzer 2 may be a blood coagulation analyzer, an immune analyzer, or a biochemical analyzer. When such device includes a cooling unit for cooling the reagent and the like, the shutdown state of the second sample analyzer 2 may be a state in which power is supplied to the input/output interface 41f, the wireless communication unit 24, and the cooling unit of the reagent, and the temperature of the cooling unit is maintained constant.

In the first to fourth embodiments described above, a configuration of executing all processing of the computer program 34a by a single computer 13a has been described above, but this is not the sole case, and a distributed system in which the processing similar to the computer program 34a is executed in a distributed manner by a plurality of devices (computers) may be adopted. This is the same for the second sample analyzer 2 and the test information management device 5.

What is claimed is:

1. A sample analyzing system comprising:
a first sample analyzer including a first measurement unit for measuring a sample, a first control unit for controlling the first measurement unit, and a storage unit for storing sample identification information for identifying the sample on which measurement is requested and order information including item information indicating an item on which the measurement is requested; and
a second sample analyzer including a second measurement unit for measuring the sample and a second control unit for controlling the second measurement unit;
wherein the first control unit is configured to transmit an activation signal for activating the second sample analyzer when a predetermined condition is met for the first sample analyzer and transmit setting information related to operation of the first sample analyzer after transmitting the activation signal;
the second control unit is configured to activate the second sample analyzer when the activation signal is received, execute setting processing for performing operation setting of the second sample analyzer based on the setting information when the setting information is received and register the order information of the second sample analyzer based on the order information contained in the received setting information when the setting information is received; and
the setting information includes the order information stored in the storage unit.

2. The sample analyzing system of claim 1, wherein the second control unit is configured to perform operation setting of the second sample analyzer under the same setting condition as the first sample analyzer based on the setting information when the setting information is received.

3. The sample analyzing system of claim 1, wherein the second control unit is configured to perform operation setting of the second sample analyzer under a condition different from the first sample analyzer based on the setting information when the setting information is received.

4. The sample analyzing system of claim 2, wherein the first control unit sets the first sample analyzer to either a first mode or a second mode different from the first mode; the second control unit sets the second sample analyzer either the first mode or the second mode; the setting information includes mode information indicating to which mode, the first mode or the second mode, the first sample analyzer is set; and the second control unit sets the second sample analyzer to either the first mode or the second mode based on the mode information contained in the received setting information.

5. The sample analyzing system of claim 2, wherein the first control unit sets the first sample analyzer to either a sampler mode for analyzing an automatically transported sample or a manual mode for analyzing a manually supplied sample; the second control unit sets the second sample analyzer to either the sampler mode or the manual mode; the setting information includes mode information indicating to which mode, the sampler mode or the manual mode, the first sample analyzer is set; and the second control unit sets the second sample analyzer to either the sampler mode or the manual mode based on the mode information contained in the received setting information.

6. The sample analyzing system of claim 1, wherein the first sample analyzer further includes an abnormality detection unit for detecting an abnormality of the first sample analyzer; and the predetermined condition includes detection of abnormality by the abnormality detection unit.

7. The sample analyzing system of claim 6, wherein the abnormality detection unit is configured to individually detect the abnormality of a plurality of items of the first sample analyzer; and the predetermined condition includes detection of abnormality of a predetermined item by the abnormality detection unit.

8. The sample analyzing system of claim 7, wherein the first control unit is configured to be able to set an abnormality item of transmitting the activation signal, and an abnormality item of not transmitting the activation signal.

9. The sample analyzing system of claim 6, wherein the first sample analyzer further includes an image display unit; the first control unit is configured to display sample information related to the sample to be moved to the second sample analyzer on the image display unit when transmitting the activation signal.

10. The sample analyzing system of claim 9, wherein the first sample analyzer further includes a transport unit for transporting a rack capable of holding a plurality of sample containers to supply the sample to the first measurement unit; and the sample information is rack identification information for identifying the rack transported to the transport unit when abnormality is detected by the abnormality detection unit.

11. The sample analyzing system of claim 1, further comprising a test information management device for registering order information with respect to the first sample analyzer and the second sample analyzer; wherein the test information management device is configured to transmit number of order notification information for notifying the number of registered order information to the first sample analyzer; and the first control unit determines whether or not the predetermined condition related to the number of registered order information is met based on the received number of order notification information when the number of order notification information is received, and transmits the activation signal when the predetermined condition is met.

12. The sample analyzing system of claim 11, wherein the first measurement unit, in which a reagent container containing reagent is installed, is configured to perform measurement of a sample using the reagent contained in the installed reagent container; the first sample analyzer further includes a reagent remaining amount storage unit for storing a remaining amount of reagent contained in the reagent container installed in the first measurement unit; and the predetermined condition includes insufficiency of remaining amount of reagent contained in the reagent container installed in the first measurement unit to execute sample analysis of the number of registered order information.

13. The sample analyzing system of claim 1 wherein the first sample analyzer includes an image display unit; the second control unit is configured to transmit activation notifying information indicating that activation is performed after executing the activation processing; and the first control unit is configured to control the image display unit to display information indicating that the second sample analyzer is not activated when the activation notifying information is not received before elapse of a predetermined time from the transmission of the activation signal.

14. The sample analyzing system of claim 1, wherein the predetermined condition includes a case in which an instruction of shutdown is received in the first sample analyzer; and when the instruction of shutdown is received for the first sample analyzer, the second control unit is configured to transmit activation notifying information indicating that activation is performed after receiving the activation signal and activating the second sample analyzer, and the first control unit is configured to shut down the first sample analyzer when the activation notifying information is received before elapse of a predetermined time from the transmission of the activation signal; and to not shut down the first sample analyzer when the activation notifying information is not received before elapse of the predetermined time from the transmission of the activation signal.

15. The sample analyzing system of claim 1, wherein the second control unit includes a reception unit for receiving an activation signal from the first control unit; the second sample analyzer is configured to take either a shutdown state in which power is not supplied to at least the second measurement unit and the reception unit is capable of receiving the activation signal or an operating state in which power is supplied to the second measurement unit; and the second sample analyzer is configured to supply power to the second measurement unit to activate the second sample analyzer and obtain the operating state when the reception unit receives the activation signal in the shutdown state.

16. A sample analyzing system comprising:
a first sample analyzer including a first measurement unit for measuring a sample and a first control unit for controlling the first measurement unit;
a second sample analyzer including a second measurement unit for measuring the sample and a second control unit for controlling the second measurement unit; and
a management device including a third control unit capable of communicating with the first control unit and the second control unit;
wherein the third control unit is configured to transmit an activation signal for activating the second sample analyzer when a predetermined condition is met for the first sample analyzer and register order information with respect to the first sample analyzer and the second sample analyzer; and
the second control unit is configured to activate the second sample analyzer when the activation signal is received; and
the predetermined condition includes number of registered order information exceeding a predetermined number.

17. The sample analyzing system of claim 16, wherein the first sample analyzer further includes an abnormality detection unit for detecting an abnormality of the first sample analyzer; and the predetermined condition includes detection of abnormality by the abnormality detection unit.

18. A sample analyzing system comprising:
a first sample analyzer including a first measurement unit for measuring a sample and a first control unit for controlling the first measurement unit;
a second sample analyzer including a second measurement unit for measuring the sample and a second control unit for controlling the second measurement unit; and
a test information management device for registering order information with respect to the first sample analyzer and the second sample analyzer;
wherein the test information management device is configured to transmit number of order notification information for notifying the number of registered order information to the first sample analyzer;
the first control unit is configured to transmit an activation signal for activating the second sample analyzer when a predetermined condition is met for the first sample analyzer, determine whether or not the predetermined condition related to the number of registered order information is met based on the received number of order notification information when the number of order notification information is received, and transmit the activation signal when the predetermined condition is met; and
the second control unit is configured to activate the second sample analyzer when the activation signal is received.

19. The sample analyzing system of claim 18, wherein the first control unit is configured to transmit setting information related to operation of the first sample analyzer after transmitting the activation signal; and
the second control unit is configured to execute setting processing for performing operation setting of the second sample analyzer based on the setting information when the setting information is received.

20. The sample analyzing system of claim 18, wherein the first measurement unit, in which a reagent container containing reagent is installed, is configured to perform measurement of a sample using the reagent contained in the installed reagent container; the first sample analyzer further includes a reagent remaining amount storage unit for storing a remaining amount of reagent contained in the reagent container installed in the first measurement unit; and the predetermined condition includes insufficiency of remaining amount of reagent contained in the reagent container installed in the first measurement unit to execute sample analysis of the number of registered order information.

21. A sample analyzing system comprising:
a first sample analyzer including a first measurement unit for measuring a sample, a first control unit for controlling the first measurement unit, and an image display unit;

a second sample analyzer including a second measurement unit for measuring the sample and a second control unit for controlling the second measurement unit;

wherein the first control unit is configured to transmit an activation signal for activating the second sample analyzer when a predetermined condition is met for the first sample analyzer;

the second control unit is configured to activate the second sample analyzer when the activation signal is received, and transmit activation notifying information indicating that activation is performed after executing the activation processing; and the first control unit is configured to control the image display unit to display information indicating that the second sample analyzer is not activated when the activation notifying information is not received before elapse of a predetermined time from the transmission of the activation signal.

22. The sample analyzing system of claim 21, wherein the first control unit is configured to transmit setting information related to operation of the first sample analyzer after transmitting the activation signal; and the second control unit is configured to execute setting processing for performing operation setting of the second sample analyzer based on the setting information when the setting information is received.

23. The sample analyzing system of claim 21, wherein the first control unit sets the first sample analyzer to either a first mode or a second mode different from the first mode; the second control unit sets the second sample analyzer to either the first mode or the second mode; the setting information includes mode information indicating to which mode, the first mode or the second mode, the first sample analyzer is set; and the second control unit sets the second sample analyzer to either the first mode or the second mode based on the mode information contained in the received setting information.

24. The sample analyzing system of claim 21, wherein the first sample analyzer further includes an abnormality detection unit for detecting an abnormality of the first sample analyzer; and the predetermined condition includes detection of abnormality by the abnormality detection unit.

25. A sample analyzing system comprising:

a first sample analyzer including a first measurement unit for measuring a sample and a first control unit for controlling the first measurement unit; and a second sample analyzer including a second measurement unit for measuring the sample and a second control unit for controlling the second measurement unit;

wherein the first control unit is configured to transmit an activation signal for activating the second sample analyzer when a predetermined condition is met for the first sample analyzer;

the second control unit is configured to activate the second sample analyzer when the activation signal is received;

the predetermined condition includes a case in which an instruction of shutdown is received in the first sample analyzer; and when the instruction of shutdown is received for the first sample analyzer, the second control unit is configured to transmit activation notifying information indicating that activation is performed after receiving the activation signal and activating the second sample analyzer; and the first control unit is configured to shut down the first sample analyzer when the activation notifying information is received before elapse of a predetermined time from the transmission of the activation signal; and to not shut down the first sample analyzer when the activation notifying information is not received before elapse of the predetermined time from the transmission of the activation signal.

26. The sample analyzing system of claim 25, wherein the first control unit is configured to transmit setting information related to operation of the first sample analyzer after transmitting the activation signal; and the second control unit is configured to execute setting processing for performing operation setting of the second sample analyzer based on the setting information when the setting information is received.

27. The sample analyzing system of claim 25, wherein the first measurement unit, in which a reagent container containing reagent is installed, is configured to perform measurement of a sample using the reagent contained in the installed reagent container; the first sample analyzer further includes a reagent remaining amount storage unit for storing a remaining amount of reagent contained in the reagent container installed in the first measurement unit; and the predetermined condition includes insufficiency of remaining amount of reagent contained in the reagent container installed in the first measurement unit to execute sample analysis of the number of registered order information.

* * * * *